(12) United States Patent
Viswanathan et al.

(10) Patent No.: US 12,721,674 B2
(45) Date of Patent: Sep. 1, 2026

(54) SYSTEMS, DEVICES, AND METHODS FOR FOCAL ABLATION

(71) Applicant: Boston Scientific Scimed, Inc., Maple Grove, MN (US)

(72) Inventors: Raju Viswanathan, Mountain View, CA (US); Gary L. Long, Cincinnati, OH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 22 days.

(21) Appl. No.: 16/828,593

(22) Filed: Mar. 24, 2020

(65) Prior Publication Data

US 2020/0397505 A1 Dec. 24, 2020

Related U.S. Application Data

(60) Provisional application No. 62/863,588, filed on Jun. 19, 2019.

(51) Int. Cl.
*A61B 18/14* (2006.01)
*A61B 34/20* (2016.01)
(Continued)

(52) U.S. Cl.
CPC .......... *A61B 18/1492* (2013.01); *A61B 34/20* (2016.02); *A61B 2017/00221* (2013.01);
(Continued)

(58) Field of Classification Search
CPC ...... A61B 18/1492; A61B 2018/00839; A61B 2018/00357; A61B 2018/1467;
(Continued)

(56) References Cited

U.S. PATENT DOCUMENTS 4,200,104 A 4/1980 Harris
4,470,407 A 9/1984 Hussein
(Continued)

FOREIGN PATENT DOCUMENTS

EP 1042990 A1 10/2000
EP 1125549 8/2001
(Continued)

OTHER PUBLICATIONS

Extended European Search Report for European Application No. 15806278.6, mailed Feb. 9, 2018, 5 pages.
(Continued)

*Primary Examiner* — Linda C Dvorak
*Assistant Examiner* — Christine A Dedoulis
(74) *Attorney, Agent, or Firm* — Nelson Mullins Riley & Scarborough LLP

(57) ABSTRACT

Systems, devices, and methods for electroporation ablation therapy are disclosed. An apparatus may include a linear shaft including a distal portion positionable near a tissue wall. The linear shaft can be configured to deflect to position the distal portion near the tissue wall. The apparatus can include a plurality of electrodes disposed on the distal portion of the linear shaft, where the plurality of electrodes are configured to generate a pulsed electric field that produces an ablation zone in the tissue wall having a depth that is independent of an orientation of the distal portion relative to the tissue wall.

30 Claims, 10 Drawing Sheets

(51) Int. Cl.
*A61B 17/00* (2006.01)
*A61B 18/00* (2006.01)
*A61N 1/362* (2006.01)

(52) U.S. Cl.
CPC ............... *A61B 2018/00357* (2013.01); *A61B 2018/00577* (2013.01); *A61B 2018/00613* (2013.01); *A61B 2018/00839* (2013.01); *A61B 2018/00988* (2013.01); *A61B 2018/1467* (2013.01); *A61B 2034/2051* (2016.02); *A61N 1/362* (2013.01)

(58) Field of Classification Search
CPC ........... A61B 2018/00613; A61B 2018/00988; A61B 2018/00577; A61N 1/362
See application file for complete search history.

(56) References Cited

U.S. PATENT DOCUMENTS 4,739,759 A 4/1988 Rexroth et al.
5,234,004 A 8/1993 Hascoet et al.
5,242,441 A 9/1993 Avitall
5,257,635 A 11/1993 Langberg
5,281,213 A 1/1994 Milder et al.
5,304,214 A 4/1994 DeFord et al.
5,306,296 A 4/1994 Wright et al.
5,334,193 A 8/1994 Nardella
5,341,807 A 8/1994 Nardella
5,342,301 A 8/1994 Saab
5,398,683 A 3/1995 Edwards et al.
5,443,463 A 8/1995 Stern et al.
5,454,370 A 10/1995 Avitall
5,515,848 A 5/1996 Corbett, III et al.
5,531,685 A 7/1996 Hemmer et al.
5,545,161 A 8/1996 Mran
5,578,040 A 11/1996 Smith
5,617,854 A 4/1997 Munsif
5,624,430 A 4/1997 Eton et al.
5,667,491 A 9/1997 Pliquett et al.
5,672,170 A 9/1997 Cho
5,700,243 A 12/1997 Narciso, Jr.
5,702,438 A 12/1997 Avitall
5,706,823 A 1/1998 Wodlinger
5,722,400 A 3/1998 Ockuly et al.
5,722,402 A 3/1998 Swanson et al.
5,749,914 A 5/1998 Janssen
5,779,699 A 7/1998 Lipson
5,788,692 A 8/1998 Campbell et al.
5,810,762 A 9/1998 Hofmann
5,833,710 A 11/1998 Jacobson
5,836,874 A 11/1998 Swanson et al.
5,836,942 A 11/1998 Netherly et al.
5,836,947 A 11/1998 Fleischman et al.
5,837,001 A * 11/1998 Mackey ............ A61B 18/1206 607/102
5,843,154 A 12/1998 Osypka
5,849,028 A 12/1998 Chen
5,860,974 A 1/1999 Abele
5,863,291 A 1/1999 Schaer
5,868,736 A 2/1999 Swanson et al.
5,871,523 A 2/1999 Fleischman et al.
5,876,336 A 3/1999 Swanson et al.
5,885,278 A 3/1999 Fleischman et al.
5,895,404 A 4/1999 Ruiz
5,899,917 A 5/1999 Edwards et al.
5,904,709 A 5/1999 Arndt et al.
5,916,158 A 6/1999 Webster, Jr.
5,916,213 A 6/1999 Haissaguerre et al.
5,921,924 A 7/1999 Avitall
5,928,269 A 7/1999 Alt
5,928,270 A 7/1999 Ramsey, III
5,938,660 A 8/1999 Swartz et al.
6,002,955 A 12/1999 Willems et al.
6,006,131 A 12/1999 Cooper et al.
6,009,351 A 12/1999 Flachman
6,014,579 A 1/2000 Pomeranz et al.
6,029,671 A 2/2000 Stevens et al.
6,033,403 A 3/2000 Tu et al.
6,035,238 A 3/2000 Ingle et al.
6,045,550 A 4/2000 Simpson et al.
6,068,653 A 5/2000 LaFontaine
6,071,274 A 6/2000 Thompson et al.
6,071,281 A 6/2000 Burnside et al.
6,074,389 A 6/2000 Levine et al.
6,076,012 A 6/2000 Swanson et al.
6,090,104 A 7/2000 Webster, Jr.
6,096,036 A 8/2000 Bowe et al.
6,113,595 A 9/2000 Muntermann
6,119,041 A 9/2000 Pomeranz et al.
6,120,500 A 9/2000 Bednarek et al.
6,142,993 A 11/2000 Whayne et al.
6,146,381 A 11/2000 Bowe et al.
6,164,283 A 12/2000 Lesh
6,167,291 A 12/2000 Barajas et al.
6,171,305 B1 1/2001 Sherman
6,216,034 B1 4/2001 Hofmann et al.
6,219,582 B1 4/2001 Hofstad et al.
6,223,085 B1 4/2001 Dann et al.
6,231,518 B1 5/2001 Grabek et al.
6,245,064 B1 6/2001 Lesh et al.
6,251,107 B1 6/2001 Schaer
6,251,109 B1 6/2001 Hasset et al.
6,251,128 B1 6/2001 Knopp et al.
6,270,476 B1 8/2001 Santoianni et al.
6,272,384 B1 8/2001 Simon et al.
6,287,306 B1 9/2001 Kroll et al.
6,314,963 B1 11/2001 Vaska et al.
6,322,559 B1 11/2001 Daulton et al.
6,350,263 B1 2/2002 Wetzig et al.
6,370,412 B1 4/2002 Armoundas et al.
6,391,024 B1 5/2002 Sun et al.
6,405,732 B1 6/2002 Edwards et al.
6,447,505 B2 9/2002 McGovern et al.
6,464,699 B1 10/2002 Swanson
6,470,211 B1 10/2002 Deker et al.
6,502,576 B1 1/2003 Lesh
6,503,247 B2 1/2003 Swartz et al.
6,517,534 B1 2/2003 McGovern et al.
6,527,724 B1 3/2003 Fenici
6,527,767 B2 3/2003 Wang et al.
6,592,581 B2 7/2003 Bowe
6,595,991 B2 7/2003 Tollner et al.
6,607,520 B2 8/2003 Keane
6,613,046 B1 9/2003 Jenkins et al.
6,623,480 B1 9/2003 Kuo et al.
6,638,278 B2 10/2003 Falwell et al.
6,666,863 B2 12/2003 Wentzel et al.
6,669,693 B2 12/2003 Friedman
6,702,811 B2 3/2004 Stewart et al.
6,719,756 B1 4/2004 Muntermann
6,723,092 B2 4/2004 Brown et al.
6,728,563 B2 4/2004 Rashidi
6,743,225 B2 6/2004 Sanchez et al.
6,743,226 B2 6/2004 Cosman et al.
6,743,239 B1 6/2004 Kuehn et al.
6,764,486 B2 7/2004 Natale
6,780,181 B2 8/2004 Kroll et al.
6,805,128 B1 10/2004 Pless
6,807,447 B2 10/2004 Griffin, III
6,892,091 B1 5/2005 Ben-Haim et al.
6,893,438 B2 5/2005 Hall et al.
6,926,714 B1 8/2005 Sra
6,955,173 B2 10/2005 Lesh
6,960,206 B2 11/2005 Keane
6,960,207 B2 11/2005 Vanney et al.
6,972,016 B2 12/2005 Hill, III et al.
6,973,339 B2 12/2005 Govari
6,979,331 B2 12/2005 Hintringer et al.
6,984,232 B2 1/2006 Vanney et al.
6,985,776 B2 1/2006 Kane et al.
7,001,383 B2 2/2006 Keidar
7,041,095 B2 5/2006 Wang et al.
7,113,831 B2 9/2006 Hooven

(56) References Cited

U.S. PATENT DOCUMENTS 7,171,263 B2 1/2007 Darvish et al.
7,182,725 B2 2/2007 Bonan et al.
7,195,628 B2 3/2007 Falkenberg
7,207,988 B2 4/2007 Leckrone et al.
7,207,989 B2 4/2007 Pike, Jr. et al.
7,229,402 B2 6/2007 Diaz et al.
7,229,437 B2 6/2007 Johnson et al.
7,250,049 B2 7/2007 Roop et al.
7,285,116 B2 10/2007 de la Rama et al.
7,285,119 B2 10/2007 Stewart et al.
7,326,208 B2 2/2008 Vanney et al.
7,346,379 B2 3/2008 Eng et al.
7,367,974 B2 5/2008 Haemmerich et al.
7,374,567 B2 5/2008 Heuser
7,387,629 B2 6/2008 Vanney et al.
7,387,630 B2 6/2008 Mest
7,387,636 B2 6/2008 Cohn et al.
7,416,552 B2 8/2008 Paul et al.
7,419,477 B2 9/2008 Simpson et al.
7,419,489 B2 9/2008 Vanney et al.
7,422,591 B2 9/2008 Phan
7,429,261 B2 9/2008 Kunis et al.
7,435,248 B2 10/2008 Taimisto et al.
7,513,896 B2 4/2009 Orszulak
7,527,625 B2 5/2009 Knight et al.
7,578,816 B2 8/2009 Boveja et al.
7,588,567 B2 9/2009 Boveja et al.
7,623,899 B2 11/2009 Worley et al.
7,678,108 B2 3/2010 Chrisitian et al.
7,681,579 B2 3/2010 Schwartz
7,771,421 B2 8/2010 Stewart et al.
7,805,182 B2 9/2010 Weese et al.
7,842,031 B2 11/2010 Abboud et al.
7,850,642 B2 12/2010 Moll et al.
7,850,685 B2 12/2010 Kunis et al.
7,857,808 B2 12/2010 Oral et al.
7,857,809 B2 12/2010 Drysen
7,869,865 B2 1/2011 Govari et al.
7,896,873 B2 3/2011 Hiller et al.
7,917,211 B2 3/2011 Zacouto
7,918,819 B2 4/2011 Karmarkar et al.
7,918,850 B2 4/2011 Govari et al.
7,922,714 B2 4/2011 Stevens-Wright
7,955,827 B2 6/2011 Rubinsky et al.
8,048,067 B2 11/2011 Davalos et al.
8,048,072 B2 11/2011 Verin et al.
8,100,895 B2 1/2012 Panos et al.
8,100,900 B2 1/2012 Prinz et al.
8,108,069 B2 1/2012 Stahler et al.
8,133,220 B2 3/2012 Lee et al.
8,137,342 B2 3/2012 Crossman
8,145,289 B2 3/2012 Calabro' et al.
8,147,486 B2 4/2012 Honour et al.
8,160,690 B2 4/2012 Wilfley et al.
8,175,680 B2 5/2012 Panescu
8,182,477 B2 5/2012 Orszulak et al.
8,206,384 B2 6/2012 Falwell et al.
8,206,385 B2 6/2012 Stangenes et al.
8,216,221 B2 7/2012 Ibrahim et al.
8,221,411 B2 7/2012 Francischelli et al.
8,226,648 B2 7/2012 Paul et al.
8,228,065 B2 7/2012 Wirtz et al.
8,235,986 B2 8/2012 Kulesa et al.
8,235,988 B2 8/2012 Davis et al.
8,251,986 B2 8/2012 Chornenky et al.
8,282,631 B2 10/2012 Davalos et al.
8,287,532 B2 10/2012 Carroll et al.
8,414,508 B2 4/2013 Thapliyal et al.
8,430,875 B2 4/2013 Ibrahim et al.
8,433,394 B2 4/2013 Harlev et al.
8,449,535 B2 5/2013 Deno et al.
8,454,594 B2 6/2013 Demarais et al.
8,463,368 B2 6/2013 Harlev et al.
8,475,450 B2 7/2013 Govari et al.
8,486,063 B2 7/2013 Werneth et al.
8,500,733 B2 8/2013 Watson
8,535,304 B2 9/2013 Sklar et al.
8,538,501 B2 9/2013 Venkatachalam et al.
8,562,588 B2 10/2013 Hobbs et al.
8,568,406 B2 10/2013 Harlev et al.
8,571,635 B2 10/2013 McGee
8,571,647 B2 10/2013 Harlev et al.
8,585,695 B2 11/2013 Shih
8,588,885 B2 11/2013 Hall et al.
8,597,288 B2 12/2013 Christian
8,608,735 B2 12/2013 Govari et al.
8,628,522 B2 1/2014 Ibrahim et al.
8,632,534 B2 1/2014 Pearson et al.
8,647,338 B2 2/2014 Chornenky et al.
8,708,952 B2 4/2014 Cohen et al.
8,734,442 B2 5/2014 Cao et al.
8,771,267 B2 7/2014 Kunis et al.
8,795,310 B2 8/2014 Fung et al.
8,808,273 B2 8/2014 Caples et al.
8,808,281 B2 8/2014 Emons et al.
8,834,461 B2 9/2014 Werneth et al.
8,834,464 B2 9/2014 Stewart et al.
8,868,169 B2 10/2014 Narayan et al.
8,876,817 B2 11/2014 Avitall et al.
8,880,195 B2 11/2014 Azure
8,886,309 B2 11/2014 Luther et al.
8,903,488 B2 12/2014 Callas et al.
8,920,411 B2 12/2014 Gelbart et al.
8,926,589 B2 1/2015 Govari
8,932,287 B2 1/2015 Gelbart et al.
8,945,117 B2 2/2015 Bencini
8,979,841 B2 3/2015 Kunis et al.
8,986,278 B2 3/2015 Fung et al.
8,996,091 B2 3/2015 de la Rama et al.
9,002,442 B2 4/2015 Harley et al.
9,005,189 B2 4/2015 Davalos et al.
9,005,194 B2 4/2015 Oral et al.
9,011,425 B2 4/2015 Fischer et al.
9,044,245 B2 6/2015 Condie et al.
9,055,959 B2 6/2015 Vaska et al.
9,072,518 B2 7/2015 Swanson
9,078,667 B2 7/2015 Besser et al.
9,101,374 B1 8/2015 Hoch et al.
9,113,911 B2 8/2015 Sherman
9,119,533 B2 9/2015 Ghaffari
9,119,634 B2 9/2015 Gelbart et al.
9,131,897 B2 9/2015 Harada et al.
9,155,590 B2 10/2015 Mathur
9,162,037 B2 10/2015 Belson et al.
9,179,972 B2 11/2015 Olson
9,186,481 B2 11/2015 Avitall et al.
9,192,769 B2 11/2015 Donofrio et al.
9,204,916 B2 12/2015 Lalonde
9,211,405 B2 12/2015 Mahapatra et al.
9,216,055 B2 12/2015 Spence et al.
9,233,248 B2 1/2016 Luther et al.
9,237,926 B2 1/2016 Nollert et al.
9,262,252 B2 2/2016 Kirkpatrick et al.
9,277,957 B2 3/2016 Long et al.
9,282,910 B2 3/2016 Narayan et al.
9,289,258 B2 3/2016 Cohen
9,289,606 B2 3/2016 Paul et al.
9,295,516 B2 3/2016 Pearson et al.
9,301,801 B2 4/2016 Scheib
9,351,789 B2 5/2016 Novichenok et al.
9,375,268 B2 6/2016 Long
9,387,031 B2 7/2016 Stewart et al.
9,414,881 B2 8/2016 Callas et al.
9,468,495 B2 10/2016 Kunis et al.
9,474,486 B2 10/2016 Eliason et al.
9,474,574 B2 10/2016 Ibrahim et al.
9,480,525 B2 11/2016 Lopes et al.
9,486,272 B2 11/2016 Bonyak et al.
9,486,273 B2 11/2016 Lopes et al.
9,492,227 B2 11/2016 Lopes et al.
9,492,228 B2 11/2016 Lopes et al.
9,510,888 B2 12/2016 Lalonde
9,517,103 B2 12/2016 Panescu et al.
9,526,573 B2 12/2016 Lopes et al.

(56) References Cited

U.S. PATENT DOCUMENTS 9,532,831 B2 1/2017 Reinders et al.
9,539,010 B2 1/2017 Gagner et al.
9,554,848 B2 1/2017 Stewart et al.
9,554,851 B2 1/2017 Sklar et al.
9,700,368 B2 7/2017 Callas et al.
9,724,170 B2 8/2017 Mickelsen
9,757,193 B2 9/2017 Zarins et al.
9,782,099 B2 10/2017 Williams et al.
9,795,442 B2 10/2017 Salahieh et al.
9,801,681 B2 10/2017 Aske et al.
9,808,304 B2 11/2017 Lalonde
9,827,036 B2 * 11/2017 Chen .................. A61B 18/1206
9,861,802 B2 1/2018 Mickelsen
9,913,685 B2 3/2018 Clark et al.
9,931,487 B2 4/2018 Quinn et al.
9,987,081 B1 6/2018 Bowers et al.
9,999,465 B2 6/2018 Long et al.
10,010,368 B2 7/2018 Laske et al.
10,016,232 B1 7/2018 Bowers et al.
10,130,423 B1 11/2018 Viswanathan et al.
10,172,673 B2 1/2019 Viswanathan et al.
10,194,818 B2 2/2019 Williams et al.
10,285,755 B2 5/2019 Stewart et al.
10,322,286 B2 6/2019 Viswanathan et al.
10,433,906 B2 10/2019 Mickelsen
10,433,908 B2 10/2019 Viswanathan et al.
10,507,302 B2 12/2019 Leeflang et al.
10,512,505 B2 12/2019 Viswanathan
10,512,779 B2 12/2019 Viswanathan et al.
10,517,672 B2 12/2019 Long
10,617,467 B2 4/2020 Viswanathan et al.
10,660,702 B2 5/2020 Viswanathan et al.
10,687,892 B2 6/2020 Long et al.
10,729,348 B2 * 8/2020 Pranaitis .................. A61B 5/25
10,893,905 B2 1/2021 Viswanathan et al.
2001/0000791 A1 5/2001 Suorsa et al.
2001/0007070 A1 7/2001 Stewart et al.
2001/0044624 A1 11/2001 Seraj et al.
2002/0052602 A1 5/2002 Wang et al.
2002/0077627 A1 6/2002 Johnson et al.
2002/0087169 A1 7/2002 Brock et al.
2002/0091384 A1 7/2002 Hooven et al.
2002/0095176 A1 7/2002 Liddicoat et al.
2002/0111618 A1 8/2002 Stewart et al.
2002/0120304 A1 8/2002 Mest
2002/0156526 A1 10/2002 Hlavka et al.
2002/0161323 A1 10/2002 Miller et al.
2002/0169445 A1 11/2002 Jain et al.
2002/0177765 A1 11/2002 Bowe et al.
2002/0183638 A1 12/2002 Swanson
2003/0014098 A1 1/2003 Quijano et al.
2003/0018374 A1 1/2003 Paulos
2003/0023287 A1 1/2003 Edwards et al.
2003/0028189 A1 2/2003 Woloszko et al.
2003/0050637 A1 3/2003 Maguire et al.
2003/0114849 A1 6/2003 Ryan
2003/0125729 A1 7/2003 Hooven et al.
2003/0130598 A1 7/2003 Manning et al.
2003/0130711 A1 7/2003 Pearson et al.
2003/0204161 A1 10/2003 Ferek Petric
2003/0204185 A1 * 10/2003 Sherman ............ A61B 18/1492
606/41
2003/0229379 A1 12/2003 Ramsey
2004/0002748 A1 1/2004 Ryan et al.
2004/0039382 A1 2/2004 Kroll et al.
2004/0049181 A1 3/2004 Stewart et al.
2004/0049182 A1 3/2004 Koblish et al.
2004/0082859 A1 4/2004 Schaer
2004/0082948 A1 4/2004 Stewart et al.
2004/0087939 A1 5/2004 Eggers et al.
2004/0111087 A1 6/2004 Stern et al.
2004/0199157 A1 10/2004 Palanker et al.
2004/0215139 A1 10/2004 Cohen
2004/0231683 A1 11/2004 Eng et al.
2004/0236360 A1 11/2004 Cohn et al.
2004/0254607 A1 12/2004 Wittenberger et al.
2004/0267337 A1 12/2004 Hayzelden
2005/0033282 A1 2/2005 Hooven
2005/0187545 A1 8/2005 Hooven et al.
2005/0222632 A1 10/2005 Obino
2005/0251130 A1 11/2005 Boveja et al.
2005/0261672 A1 11/2005 Deem et al.
2005/0288730 A1 12/2005 Deem et al.
2006/0009755 A1 1/2006 Sra
2006/0009759 A1 1/2006 Chrisitian et al.
2006/0015095 A1 1/2006 Desinger et al.
2006/0015165 A1 1/2006 Bertolero et al.
2006/0024359 A1 2/2006 Walker et al.
2006/0058781 A1 3/2006 Long
2006/0111702 A1 5/2006 Oral et al.
2006/0142801 A1 6/2006 Demarais et al.
2006/0167448 A1 7/2006 Kozel
2006/0217703 A1 9/2006 Chornenky et al.
2006/0241734 A1 10/2006 Marshall et al.
2006/0264752 A1 11/2006 Rubinsky et al.
2006/0270900 A1 11/2006 Chin et al.
2006/0287648 A1 12/2006 Schwartz
2006/0293730 A1 12/2006 Rubinsky et al.
2006/0293731 A1 12/2006 Rubinsky et al.
2007/0005053 A1 1/2007 Dando
2007/0021744 A1 1/2007 Creighton
2007/0060989 A1 3/2007 Deem et al.
2007/0066972 A1 3/2007 Ormsby et al.
2007/0083192 A1 4/2007 Welch
2007/0129721 A1 6/2007 Phan et al.
2007/0129760 A1 6/2007 Demarais et al.
2007/0156135 A1 7/2007 Rubinsky et al.
2007/0167740 A1 7/2007 Grunewald et al.
2007/0167940 A1 7/2007 Stevens-Wright
2007/0173878 A1 7/2007 Heuser
2007/0208329 A1 9/2007 Ward et al.
2007/0225589 A1 9/2007 Viswanathan
2007/0249923 A1 10/2007 Keenan
2007/0260223 A1 11/2007 Scheibe et al.
2007/0270792 A1 11/2007 Hennemann et al.
2008/0009855 A1 1/2008 Hamou
2008/0033426 A1 2/2008 Machell
2008/0065061 A1 3/2008 Viswanathan
2008/0086120 A1 4/2008 Mirza et al.
2008/0091195 A1 4/2008 Silwa et al.
2008/0103545 A1 5/2008 Bolea et al.
2008/0132885 A1 6/2008 Rubinsky et al.
2008/0161789 A1 7/2008 Thao et al.
2008/0172048 A1 7/2008 Martin et al.
2008/0200913 A1 8/2008 Viswanathan
2008/0208118 A1 8/2008 Goldman
2008/0243214 A1 10/2008 Koblish
2008/0281322 A1 11/2008 Sherman et al.
2008/0300574 A1 12/2008 Belson et al.
2008/0300588 A1 12/2008 Groth et al.
2009/0024084 A1 1/2009 Khosla et al.
2009/0048591 A1 2/2009 Brahim et al.
2009/0062788 A1 3/2009 Long et al.
2009/0076500 A1 3/2009 Azure
2009/0105654 A1 4/2009 Kurth et al.
2009/0138009 A1 5/2009 Viswanathan et al.
2009/0149917 A1 6/2009 Whitehurst et al.
2009/0163905 A1 6/2009 Winkler et al.
2009/0171352 A1 7/2009 Sutter
2009/0182287 A1 7/2009 Kassab
2009/0228003 A1 9/2009 Sinelnikov
2009/0240248 A1 9/2009 Deford et al.
2009/0275827 A1 11/2009 Aiken et al.
2009/0281477 A1 11/2009 Mikus et al.
2009/0306651 A1 12/2009 Schneider
2010/0004623 A1 1/2010 Hamilton et al.
2010/0023004 A1 1/2010 Francischelli et al.
2010/0137861 A1 6/2010 Soroff et al.
2010/0185140 A1 7/2010 Kassab et al.
2010/0185186 A1 7/2010 Longoria
2010/0191112 A1 7/2010 Demarais et al.
2010/0191232 A1 7/2010 Boveda
2010/0204560 A1 8/2010 Salahieh et al.
2010/0241185 A1 9/2010 Mahapatra et al.

(56) References Cited

U.S. PATENT DOCUMENTS

2010/0261994 A1 10/2010 Davalos et al.
2010/0274238 A1 10/2010 Klimovitch
2010/0280513 A1 11/2010 Juergen et al.
2010/0280539 A1 11/2010 Miyoshi et al.
2010/0292687 A1 11/2010 Kauphusman et al.
2010/0312096 A1 12/2010 Guttman et al.
2010/0312300 A1 12/2010 Ryu et al.
2011/0028962 A1 2/2011 Werneth et al.
2011/0028964 A1 2/2011 Edwards
2011/0040199 A1 2/2011 Hopenfeld
2011/0098694 A1 4/2011 Long
2011/0106221 A1 5/2011 Neal, II et al.
2011/0130708 A1 6/2011 Perry et al.
2011/0144524 A1 6/2011 Fish et al.
2011/0144633 A1 6/2011 Govari
2011/0160785 A1 6/2011 Mori et al.
2011/0190659 A1 8/2011 Long et al.
2011/0190727 A1 8/2011 Edmunds et al.
2011/0213231 A1 9/2011 Hall et al.
2011/0276047 A1 11/2011 Sklar et al.
2011/0276075 A1 11/2011 Fung et al.
2011/0288544 A1 11/2011 Verin et al.
2011/0288547 A1 11/2011 Morgan et al.
2011/0301587 A1 12/2011 Deem et al.
2011/0313417 A1 12/2011 De La Rama et al.
2012/0029512 A1 2/2012 Willard et al.
2012/0046570 A1 2/2012 Villegas et al.
2012/0053581 A1 3/2012 Wittkampf et al.
2012/0059255 A1 3/2012 Paul et al.
2012/0071872 A1 3/2012 Rubinsky et al.
2012/0078320 A1 3/2012 Schotzko et al.
2012/0078343 A1 3/2012 Fish
2012/0089089 A1 4/2012 Swain et al.
2012/0095459 A1 4/2012 Callas et al.
2012/0101413 A1 4/2012 Beetel et al.
2012/0158021 A1 6/2012 Morrill
2012/0165667 A1 6/2012 Altmann et al.
2012/0172859 A1 7/2012 Condie et al.
2012/0172867 A1 7/2012 Ryu et al.
2012/0197100 A1 8/2012 Razavi et al.
2012/0209260 A1 8/2012 Lambert et al.
2012/0220998 A1 8/2012 Long et al.
2012/0265198 A1 10/2012 Crow et al.
2012/0283582 A1 11/2012 Mahapatra et al.
2012/0303019 A1 11/2012 Zhao et al.
2012/0310052 A1 12/2012 Mahapatra et al.
2012/0310230 A1 12/2012 Willis
2012/0310237 A1 12/2012 Swanson
2012/0316557 A1 12/2012 Sartor et al.
2013/0030430 A1 1/2013 Stewart et al.
2013/0060247 A1 3/2013 Sklar et al.
2013/0060248 A1 3/2013 Sklar et al.
2013/0079768 A1 3/2013 De Luca et al.
2013/0090651 A1 4/2013 Smith
2013/0096655 A1 4/2013 Moffitt et al.
2013/0103027 A1 4/2013 Sklar et al.
2013/0103064 A1 4/2013 Arenson et al.
2013/0123778 A1 5/2013 Richardson et al.
2013/0131662 A1 5/2013 Wittkampf
2013/0158538 A1 6/2013 Govari
2013/0158621 A1 6/2013 Ding et al.
2013/0172715 A1 7/2013 Just et al.
2013/0172864 A1 7/2013 Ibrahim et al.
2013/0172875 A1 7/2013 Govari et al.
2013/0184702 A1 7/2013 Neal, II et al.
2013/0218157 A1 8/2013 Callas et al.
2013/0226174 A1 8/2013 Brahim et al.
2013/0237984 A1 9/2013 Sklar
2013/0253415 A1 9/2013 Sano et al.
2013/0296679 A1 11/2013 Condie et al.
2013/0310829 A1 11/2013 Cohen
2013/0317385 A1 11/2013 Sklar et al.
2013/0331831 A1 12/2013 Werneth et al.
2013/0338467 A1 12/2013 Grasse et al.
2014/0005664 A1 1/2014 Govari et al.
2014/0024911 A1 1/2014 Harlev et al.
2014/0039288 A1 2/2014 Shih
2014/0051993 A1 2/2014 McGee
2014/0052118 A1 2/2014 Laske et al.
2014/0052126 A1 2/2014 Long et al.
2014/0052216 A1 2/2014 Long et al.
2014/0058377 A1 2/2014 Deem et al.
2014/0081113 A1 3/2014 Cohen et al.
2014/0100563 A1 4/2014 Govari et al.
2014/0107644 A1 4/2014 Falwell et al.
2014/0142408 A1 5/2014 De La Rama et al.
2014/0148804 A1 5/2014 Ward et al.
2014/0163480 A1 6/2014 Govari et al.
2014/0163546 A1 6/2014 Govari et al.
2014/0171942 A1 6/2014 Werneth et al.
2014/0180035 A1 6/2014 Anderson
2014/0187916 A1 7/2014 Clark et al.
2014/0194716 A1 7/2014 Diep et al.
2014/0194867 A1 7/2014 Fish et al.
2014/0200567 A1 7/2014 Cox et al.
2014/0235986 A1 8/2014 Harlev et al.
2014/0235988 A1 8/2014 Ghosh
2014/0235989 A1 8/2014 Wodlinger et al.
2014/0243851 A1 8/2014 Cohen et al.
2014/0257130 A1* 9/2014 Cao .................... A61B 18/1492 600/549
2014/0276760 A1 9/2014 Bonyak et al.
2014/0276782 A1 9/2014 Paskar
2014/0276791 A1 9/2014 Ku et al.
2014/0288556 A1 9/2014 Ibrahim et al.
2014/0303721 A1 10/2014 Fung et al.
2014/0330266 A1 11/2014 Thompson et al.
2014/0343549 A1 11/2014 Spear et al.
2014/0364845 A1 12/2014 Rashidi
2014/0371613 A1 12/2014 Narayan et al.
2015/0005767 A1 1/2015 Werneth et al.
2015/0011995 A1 1/2015 Avitall et al.
2015/0066108 A1 3/2015 Shi et al.
2015/0119674 A1 4/2015 Fischell et al.
2015/0126840 A1 5/2015 Thakur et al.
2015/0133914 A1 5/2015 Koblish
2015/0138977 A1 5/2015 Dacosta
2015/0141978 A1 5/2015 Subramaniam et al.
2015/0141982 A1 5/2015 Lee
2015/0142041 A1 5/2015 Kendale et al.
2015/0148796 A1 5/2015 Bencini
2015/0150472 A1 6/2015 Harlev et al.
2015/0157402 A1 6/2015 Kunis et al.
2015/0157412 A1 6/2015 Wallace et al.
2015/0164584 A1 6/2015 Davalos et al.
2015/0173824 A1 6/2015 Davalos et al.
2015/0173828 A1 6/2015 Avitall
2015/0174404 A1 6/2015 Rousso et al.
2015/0182740 A1 7/2015 Mickelsen
2015/0196217 A1 7/2015 Harlev et al.
2015/0223726 A1 8/2015 Harlev et al.
2015/0230699 A1 8/2015 Berul et al.
2015/0258344 A1 9/2015 Tandri et al.
2015/0265342 A1 9/2015 Long et al.
2015/0265344 A1 9/2015 Aktas et al.
2015/0272656 A1 10/2015 Chen
2015/0272664 A9 10/2015 Cohen
2015/0272667 A1 10/2015 Govari et al.
2015/0282729 A1 10/2015 Harlev et al.
2015/0289923 A1 10/2015 Davalos et al.
2015/0304879 A1 10/2015 Dacosta
2015/0320481 A1 11/2015 Cosman et al.
2015/0321021 A1 11/2015 Tandri et al.
2015/0342532 A1 12/2015 Basu et al.
2015/0343212 A1 12/2015 Rousso et al.
2015/0351836 A1 12/2015 Prutchi
2015/0359583 A1 12/2015 Swanson
2016/0000500 A1 1/2016 Salahieh et al.
2016/0008061 A1 1/2016 Fung et al.
2016/0008065 A1 1/2016 Gliner et al.
2016/0029960 A1 2/2016 Toth et al.
2016/0038772 A1 2/2016 Thapliyal et al.
2016/0051204 A1 2/2016 Harlev et al.
2016/0051324 A1 2/2016 Stewart et al.

(56) References Cited

U.S. PATENT DOCUMENTS

2016/0058493 A1 3/2016 Neal, II et al.
2016/0058506 A1 3/2016 Spence et al.
2016/0066993 A1 3/2016 Avitall et al.
2016/0074679 A1 3/2016 Thapliyal et al.
2016/0095531 A1 4/2016 Narayan et al.
2016/0095642 A1 4/2016 Deno et al.
2016/0095653 A1 4/2016 Lambert et al.
2016/0100797 A1 4/2016 Mahapatra et al.
2016/0100884 A1 4/2016 Fay et al.
2016/0106498 A1 4/2016 Highsmith et al.
2016/0106500 A1 4/2016 Olson
2016/0113709 A1 4/2016 Maor
2016/0113712 A1 4/2016 Cheung et al.
2016/0120564 A1 5/2016 Kirkpatrick et al.
2016/0128770 A1 5/2016 Afonso et al.
2016/0166167 A1 6/2016 Narayan et al.
2016/0166310 A1 6/2016 Stewart et al.
2016/0166311 A1 6/2016 Long et al.
2016/0174865 A1 6/2016 Stewart et al.
2016/0183877 A1 6/2016 Williams et al.
2016/0184003 A1 6/2016 Srimathveeravalli et al.
2016/0184004 A1 6/2016 Hull et al.
2016/0213282 A1 7/2016 Leo et al.
2016/0220307 A1 8/2016 Miller et al.
2016/0235470 A1 8/2016 Callas et al.
2016/0249972 A1 9/2016 Klink
2016/0256682 A1 9/2016 Paul et al.
2016/0287314 A1 10/2016 Arena et al.
2016/0310211 A1 10/2016 Long
2016/0324564 A1 11/2016 Gerlach et al.
2016/0324573 A1 11/2016 Mickelsen et al.
2016/0331254 A1 11/2016 Tegg et al.
2016/0331441 A1 11/2016 Konings
2016/0331459 A1 11/2016 Townley et al.
2016/0338770 A1 11/2016 Bar-Tal et al.
2016/0354142 A1 12/2016 Pearson et al.
2016/0361109 A1 12/2016 Weaver et al.
2017/0001016 A1 1/2017 De Ridder
2017/0035499 A1 2/2017 Stewart et al.
2017/0042449 A1 2/2017 Deno et al.
2017/0042615 A1 2/2017 Salahieh et al.
2017/0056648 A1 3/2017 Syed et al.
2017/0065330 A1 3/2017 Mickelsen et al.
2017/0065339 A1 3/2017 Mickelsen
2017/0065340 A1 3/2017 Long
2017/0065343 A1 3/2017 Mickelsen
2017/0071543 A1 3/2017 Basu et al.
2017/0095291 A1 4/2017 Harrington et al.
2017/0105793 A1 4/2017 Cao et al.
2017/0120048 A1 5/2017 He et al.
2017/0146584 A1 5/2017 Daw et al.
2017/0151014 A1 6/2017 Perfler
2017/0151029 A1 6/2017 Mickelsen
2017/0172654 A1 6/2017 Wittkampf et al.
2017/0172666 A1* 6/2017 Govari .................... A61B 8/12
2017/0181795 A1 6/2017 Debruyne
2017/0189097 A1 7/2017 Viswanathan et al.
2017/0215953 A1 8/2017 Long et al.
2017/0245928 A1 8/2017 Xiao et al.
2017/0246455 A1 8/2017 Athos et al.
2017/0312024 A1 11/2017 Harlev et al.
2017/0312025 A1 11/2017 Harlev et al.
2017/0312027 A1 11/2017 Harlev et al.
2018/0001056 A1 1/2018 Leeflang et al.
2018/0028252 A1 2/2018 Lalonde
2018/0042674 A1 2/2018 Mickelsen
2018/0042675 A1 2/2018 Long
2018/0043153 A1 2/2018 Viswanathan et al.
2018/0064359 A1 3/2018 Pranaitis et al.
2018/0064488 A1 3/2018 Long et al.
2018/0085160 A1* 3/2018 Viswanathan ......... A61N 1/327
2018/0093088 A1 4/2018 Mickelsen
2018/0133460 A1 5/2018 Townley et al.
2018/0161093 A1 6/2018 Basu et al.
2018/0168511 A1 6/2018 Hall et al.
2018/0184982 A1* 7/2018 Basu .................... A61B 5/6858
2018/0193090 A1 7/2018 de la Rama et al.
2018/0200497 A1 7/2018 Mickelsen
2018/0235496 A1 8/2018 Wu et al.
2018/0256109 A1 9/2018 Wu et al.
2018/0280080 A1 10/2018 Govari et al.
2018/0303488 A1 10/2018 Hill
2018/0303543 A1* 10/2018 Stewart .............. A61B 18/1492
2018/0311497 A1 11/2018 Viswanathan et al.
2018/0344202 A1 12/2018 Bar-Tal et al.
2018/0344393 A1 12/2018 Gruba et al.
2018/0360531 A1 12/2018 Holmes et al.
2018/0360534 A1* 12/2018 Teplitsky ............. A61B 5/0084
2019/0015007 A1 1/2019 Rottmann et al.
2019/0015638 A1 1/2019 Gruba et al.
2019/0030328 A1 1/2019 Stewart et al.
2019/0046791 A1 2/2019 Ebbers et al.
2019/0069950 A1 3/2019 Viswanathan et al.
2019/0076179 A1 3/2019 Babkin et al.
2019/0125439 A1 5/2019 Rohl et al.
2019/0125788 A1 5/2019 Gruba et al.
2019/0143106 A1 5/2019 Dewitt et al.
2019/0151015 A1 5/2019 Viswanathan et al.
2019/0175263 A1 6/2019 Altmann et al.
2019/0183378 A1 6/2019 Mosesov et al.
2019/0183567 A1 6/2019 Govari et al.
2019/0192223 A1 6/2019 Rankin
2019/0201089 A1 7/2019 Waldstreicher et al.
2019/0201688 A1 7/2019 Olson
2019/0209235 A1 7/2019 Stewart et al.
2019/0223948 A1 7/2019 Stewart et al.
2019/0223949 A1* 7/2019 Coates ................. A61N 1/0529
2019/0231421 A1 8/2019 Viswanathan et al.
2019/0231425 A1 8/2019 Waldstreicher et al.
2019/0254735 A1 8/2019 Stewart et al.
2019/0269912 A1 9/2019 Viswanathan et al.
2019/0298442 A1 10/2019 Ogata et al.
2019/0307500 A1* 10/2019 Byrd .................. A61B 18/1492
2019/0336198 A1 11/2019 Viswanathan et al.
2019/0336207 A1 11/2019 Viswanathan
2019/0350647 A1 11/2019 Ramberg et al.
2019/0350649 A1 11/2019 Sutermeister et al.
2020/0008869 A1 1/2020 Byrd
2020/0008870 A1 1/2020 Gruba et al.
2020/0009378 A1 1/2020 Stewart et al.
2020/0038104 A1 2/2020 Mickelsen
2020/0046423 A1 2/2020 Viswanathan et al.
2020/0093539 A1 3/2020 Long et al.
2020/0289197 A1 9/2020 Viswanathan et al.
2021/0220038 A1* 7/2021 Kenneth ............ A61B 18/1402

FOREIGN PATENT DOCUMENTS

EP 0797956 6/2003
EP 1127552 6/2006
EP 1340469 3/2007
EP 1009303 6/2009
EP 2213729 8/2010
EP 2425871 3/2012
EP 1803411 8/2012
EP 2532320 A2 12/2012
EP 2587275 5/2013
EP 2663227 11/2013
EP 1909678 1/2014
EP 2217165 3/2014
EP 2376193 3/2014
EP 2708181 3/2014
EP 2777579 A1 9/2014
EP 2934307 10/2015
EP 2777585 6/2016
EP 2382935 B1 3/2018
EP 3111871 B1 3/2018
EP 3151773 B1 4/2018
EP 3056242 B1 7/2018
JP H06-507797 9/1994
JP H10-510745 10/1998
JP 2000-508196 7/2000
JP 2005-516666 6/2005
JP 2006-506184 2/2006

(56) References Cited

FOREIGN PATENT DOCUMENTS

| | | |
|---|---|---|
| JP | 2007-325935 | 12/2007 |
| JP | 2008-538997 | 11/2008 |
| JP | 2009-500129 | 1/2009 |
| JP | 2011-509158 | 3/2011 |
| JP | 2012-050538 | 3/2012 |
| WO | WO 92/07622 | 5/1992 |
| WO | WO 92/21278 | 12/1992 |
| WO | WO 92/21285 | 12/1992 |
| WO | WO 94/07413 | 4/1994 |
| WO | WO 97/24073 | 7/1997 |
| WO | WO 97/25917 | 7/1997 |
| WO | WO 97/37719 | 10/1997 |
| WO | WO 1999/004851 | 2/1999 |
| WO | WO 1999/022659 | 5/1999 |
| WO | WO 1999/049407 | 9/1999 |
| WO | WO 1999/056650 | 11/1999 |
| WO | WO 1999/059486 | 11/1999 |
| WO | WO 2002/056782 | 7/2002 |
| WO | WO 2003/053289 | 7/2003 |
| WO | WO 2003/065916 | 8/2003 |
| WO | WO 2004/045442 | 6/2004 |
| WO | WO 2004/086994 | 10/2004 |
| WO | WO 2005/046487 | 5/2005 |
| WO | WO 2006/115902 | 11/2006 |
| WO | WO 2007/006055 | 1/2007 |
| WO | WO 2007/079438 | 7/2007 |
| WO | WO 2009/082710 | 7/2009 |
| WO | WO 2009/089343 | 7/2009 |
| WO | WO 2009/137800 | 11/2009 |
| WO | WO 2010/014480 | 2/2010 |
| WO | WO 2011/028310 | 3/2011 |
| WO | WO 2011/154805 | 12/2011 |
| WO | WO 2012/051433 | 4/2012 |
| WO | WO 2012/145073 | 10/2012 |
| WO | WO 2012/153928 | 11/2012 |
| WO | WO 2013/019385 | 2/2013 |
| WO | WO 2014/025394 | 2/2014 |
| WO | WO 2014/031800 | 2/2014 |
| WO | WO 2014/036439 | 3/2014 |
| WO | WO 2014/160832 | 10/2014 |
| WO | WO 2015/066322 | 5/2015 |
| WO | WO 2015/099786 | 7/2015 |
| WO | WO 2015/103530 | 7/2015 |
| WO | WO 2015/103574 | 7/2015 |
| WO | WO 2015/130824 | 9/2015 |
| WO | WO 2015/140741 | 9/2015 |
| WO | WO 2015/143327 | 9/2015 |
| WO | WO 2015/171921 | 11/2015 |
| WO | WO 2015/175944 | 11/2015 |
| WO | WO 2015/192018 | 12/2015 |
| WO | WO 2015/192027 | 12/2015 |
| WO | WO 2016/059027 | 4/2016 |
| WO | WO 2016/060983 | 4/2016 |
| WO | WO 2016/081650 | 5/2016 |
| WO | WO 2016/090175 | 6/2016 |
| WO | WO 2017/093926 | 6/2017 |
| WO | WO 2017/119934 | 7/2017 |
| WO | WO 2017/120169 | 7/2017 |
| WO | WO 2017/192477 | 11/2017 |
| WO | WO 2017/192495 | 11/2017 |
| WO | WO 2017/201504 | 11/2017 |
| WO | WO 2017/218734 | 12/2017 |
| WO | WO 2018/005511 | 1/2018 |
| WO | WO 2018/106569 | 6/2018 |
| WO | WO 2018/200800 | 11/2018 |
| WO | WO 2019/023259 | 1/2019 |
| WO | WO 2019/023280 | 1/2019 |
| WO | WO 2019/035071 | 2/2019 |
| WO | WO 2019/133606 | 7/2019 |
| WO | WO 2019/133608 | 7/2019 |
| WO | WO 2019/136218 | 7/2019 |
| WO | WO 2019/181612 | 9/2019 |
| WO | WO 2019/234133 | 12/2019 |
| WO | 2020/257207 A1 | 12/2020 |

OTHER PUBLICATIONS

International Search Report and Written Opinion for International Application No. PCT/US2015/035592, mailed Oct. 2, 2015, 13 pages.
Extended European Search Report for European Application No. 17736218.3 mailed Aug. 23, 2019, 9 pages.
International Search Report and Written Opinion for International Application No. PCT/US2017/012099, mailed May 18, 2017, 17 pages.
Office Action for U.S. Appl. No. 15/711,266, mailed Feb. 23, 2018, 14 pages.
International Search Report and Written Opinion for International Application No. PCT/US2018/029938, mailed Aug. 29, 2018, 14 pages.
Office Action for U.S. Appl. No. 16/181,027, mailed Sep. 4, 2019, 12 pages.
International Search Report and Written Opinion for International Application No. PCT/US2019/014226, mailed Apr. 29, 2019, 15 pages.
Office Action for U.S. Appl. No. 16/240,066, mailed May 29, 2019, 7 pages.
Office Action for U.S. Appl. No. 16/375,561, mailed Oct. 17, 2019, 15 pages.
Office Action for U.S. Appl. No. 16/595,250, mailed Mar. 16, 2020, 7 pages.
International Search Report and Written Opinion for International Application No. PCT/US2018/050660, mailed Nov. 26, 2018, 13 pages.
International Search Report and Written Opinion for International Application No. PCT/US2019/051998, mailed Feb. 26, 2020, 11 pages.
Du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Safety and Feasibility of Closed Chest Epicardial Catheter Ablation Using Electroporation," Circ Arrhythm Electrophysiol., 7:913-919 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).
International Search Report and Written Opinion for International Application No. PCT/US2020/026682, mailed Jun. 16, 2020, 10 pages.
Office Action for U.S. Appl. No. 16/817,410, mailed Jul. 16, 2020, 23 pages.
International Search Report and Written Opinion for International Application No. PCT/US2020/037948, mailed Jul. 20, 2020, 16 pages.
First Office Action for Chinese Application No. 201780005770.7, dated Sep. 27, 2020, 8 pages.

(56) References Cited

OTHER PUBLICATIONS

Notice of Reasons for Rejection for Japanese Application No. 2018-534873, mailed Oct. 16, 2020, 7 pages.
Extended European Search Report for European Application No. 18790020.4, mailed Feb. 2, 2021, 9 pages.
Office Action for U.S. Appl. No. 16/886,514, mailed Nov. 20, 2020, 11 pages.
Extended European Search Report and Search Opinion received for European Application No. 26155584.1, mailed on Apr. 23, 2026, 7 pages.

* cited by examiner

SYSTEMS, DEVICES, AND METHODS FOR FOCAL ABLATION

CROSS REFERENCE TO RELATED APPLICATIONS

This application claims the benefit of U.S. Provisional Application No. 62/863,588, filed on Jun. 19, 2019, titled "SYSTEMS, DEVICES, AND METHODS FOR FOCAL ABLATION," the entire disclosure of which is incorporated herein by reference in its entirety.

BACKGROUND

The generation of pulsed electric fields for tissue therapeutics has moved from the laboratory to clinical applications over the past two decades, while the effects of brief pulses of high voltages and large electric fields on tissue have been investigated for the past forty years or more. Application of brief high DC voltages to tissue may generate locally high electric fields typically in the range of hundreds of volts per centimeter that disrupt cell membranes by generating pores in the cell membrane. While the precise mechanism of this electrically-driven pore generation or electroporation continues to be studied, it is thought that the application of relatively brief and large electric fields generates instabilities in the lipid bilayers in cell membranes, causing the occurrence of a distribution of local gaps or pores in the cell membrane. This electroporation may be irreversible if the applied electric field at the membrane is larger than a threshold value such that the pores do not close and remain open, thereby permitting exchange of biomolecular material across the membrane leading to necrosis and/or apoptosis (cell death). Subsequently, the surrounding tissue may heal naturally.

While pulsed DC voltages may drive electroporation under the right circumstances, there remains an unmet need for thin, flexible, atraumatic devices that effectively deliver high DC voltage electroporation ablation therapy selectively to endocardial tissue in regions of interest while minimizing damage to healthy tissue.

SUMMARY

Described here are systems, devices, and methods for ablating tissue through irreversible electroporation. Generally, a device (e.g., a catheter) for the application of pulsed electric field ablation to soft tissue (e.g., cardiac tissue) can include a linear flexible body with a plurality of distally placed electrodes. In some embodiments, the device can be used to form focal ablation lesions.

In some embodiments, a system includes an ablation device and a signal generator. The ablation device including: a linear shaft including a distal portion positionable near a tissue wall, the linear shaft configured to deflect to position the distal portion near the tissue wall; a plurality of electrodes disposed on the distal portion, the plurality of electrodes including: a set of distal electrodes; and a set of proximal electrodes disposed proximal to the set of distal electrodes, each proximal electrode from the set of proximal electrodes spaced from an adjacent proximal electrode from the set of proximal electrodes by a first length of the linear shaft, a distal most proximal electrode from the set of proximal electrodes spaced from a proximal most distal electrode from the set of distal electrodes by a second length of the linear shaft; and a plurality of leads coupled to the plurality of electrodes, each lead having insulation configured to withstand a potential difference of at least about 700 V without dielectric breakdown. The signal generator being operatively coupled to the ablation device and configured to activate at least one distal electrode from the set of distal electrodes with a first polarity and the set of proximal electrodes with a second polarity opposite the first polarity such that the plurality of electrodes generates pulsed electric field energy that produces an ablation zone in the tissue wall having a depth that is independent of an orientation of the distal portion relative to the tissue wall.

In some embodiments, an apparatus includes: a linear shaft including a distal portion positionable near a tissue wall, the linear shaft configured to deflect to position the distal portion near the tissue wall; a plurality of electrodes disposed on the distal portion, the plurality of electrodes configured to generate a pulsed electric field that produces an ablation zone in the tissue wall having a depth that is independent of an orientation of the distal portion relative to the tissue wall, the plurality of electrodes including: a set of distal electrodes including a distal tip electrode disposed at a tip of the linear shaft; and a set of proximal electrodes disposed proximal to the set of distal electrodes, each proximal electrode from the set of proximal electrodes spaced from an adjacent proximal electrode from the set of proximal electrodes by a first length of the linear shaft, a distal most proximal electrode from the set of proximal electrodes spaced from a proximal most distal electrode from the set of distal electrodes by a second length of the linear shaft, the first length of the linear shaft being less than the second length of the linear shaft; and a plurality of leads coupled to the plurality of electrodes, each lead from the plurality of leads configured to deliver a voltage output having an amplitude of at least 700V to the plurality of electrodes (1) without dielectric breakdown of its corresponding insulation and (2) such that the set of distal electrodes are activated with a first polarity and the set of proximal electrodes are activated with a second polarity opposite the first polarity to collectively generate the pulsed electric field.

In some embodiments, a method includes: positioning a linear shaft of an ablation device in a cardiac chamber of a heart of a subject such that a distal portion of the linear shaft is near a tissue wall, the ablation device including a plurality of electrodes disposed on the distal portion, the plurality of electrodes including a set of distal electrodes and a set of proximal electrodes, each proximal electrode from the set of proximal electrodes spaced from an adjacent proximal electrode from the set of proximal electrodes by a first length of the linear shaft, a distal most proximal electrode from the set of proximal electrodes spaced from a proximal most distal electrode from the set of distal electrodes by a second length of the linear shaft; and generating, using a signal generator, a pulse waveform having a voltage amplitude of at least about 700 V; delivering a pulse waveform having a first polarity to the set of distal electrodes and a pulse waveform having a second polarity opposite to the first polarity to the set of proximal electrodes such that the plurality of electrodes collectively generates a pulsed electric field that produces an ablation zone in the tissue wall having a depth that is independent of an orientation of the distal portion relative to the tissue wall.

DETAILED DESCRIPTION

Described herein are systems, devices, and methods for application of pulsed electric fields to ablate tissue by irreversible electroporation. In some embodiments, systems, devices, and methods described herein can be configured to provide focal ablation. Such systems, devices, and methods can generate a controllable ablation zone within tissue in an orientation-independent matter, i.e., generally independent of an orientation of the ablation device (e.g., catheter) relative to a tissue surface or wall.

The term "electroporation" as used herein refers to the application of an electric field to a cell membrane to change the permeability of the cell membrane to the extracellular environment. The term "reversible electroporation" as used herein refers to the application of an electric field to a cell membrane to temporarily change the permeability of the cell membrane to the extracellular environment. For example, a cell undergoing reversible electroporation can observe the temporary and/or intermittent formation of one or more pores in its cell membrane that close up upon removal of the electric field. The term "irreversible electroporation" as used herein refers to the application of an electric field to a cell membrane to permanently change the permeability of the cell membrane to the extracellular environment. For example, a cell undergoing irreversible electroporation can observe the formation of one or more pores in its cell membrane that persist upon removal of the electric field.

Figure 1:
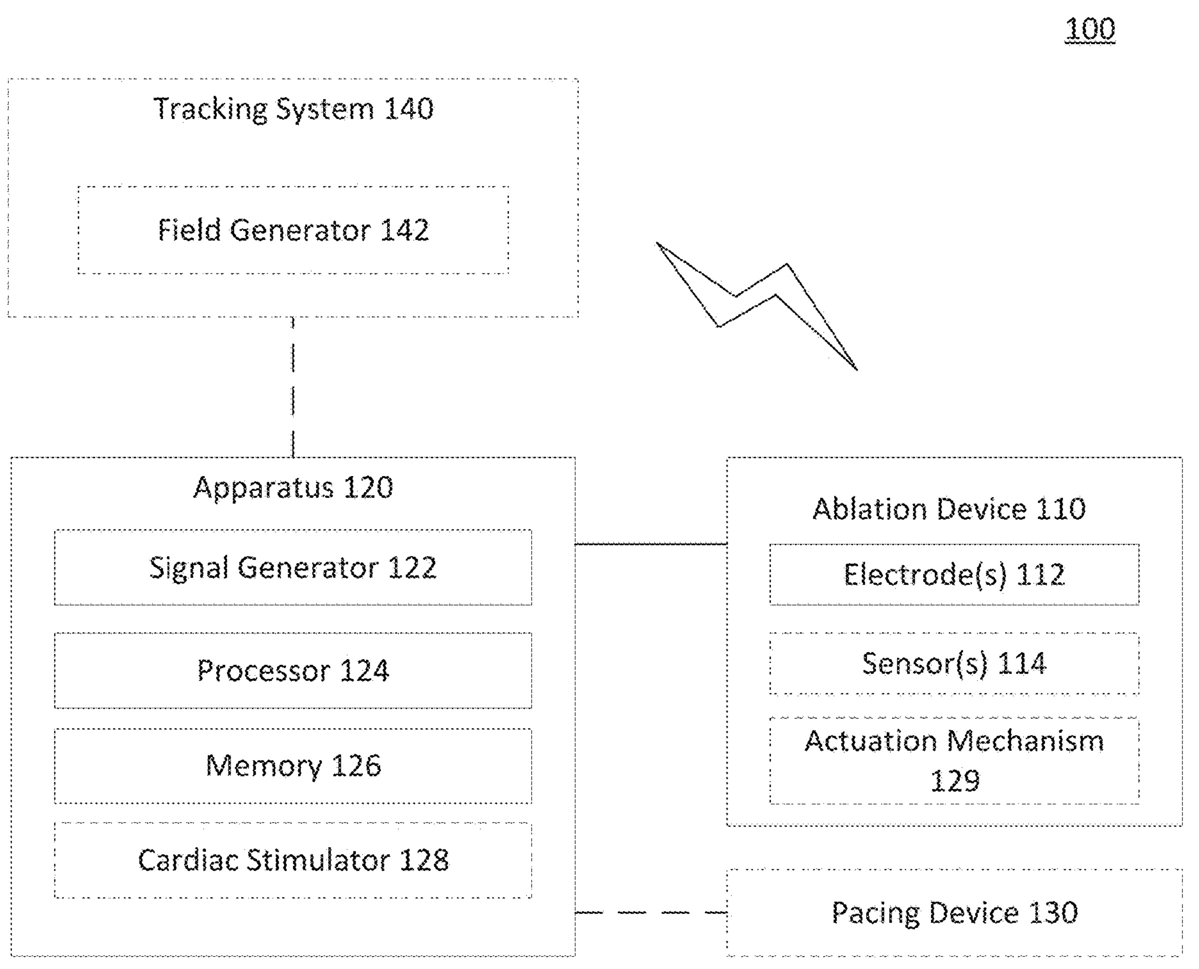
FIG. 1 is a block diagram of an electroporation system, according to embodiments.

Generally, the systems and devices described herein include one or more ablation devices (e.g., catheters) configured to ablate tissue, e.g., in a chamber (e.g., atrial, ventricular) of a heart. FIG. 1 illustrates an ablation system (100). The system (100) may include an apparatus (120) including a signal generator (122), processor (124), memory (126), and optionally a cardiac stimulator (128). The apparatus (120) may be coupled to an ablation device (110) and optionally to a pacing device (130).

The signal generator (122) may be configured to generate voltage pulse waveforms for irreversible electroporation of tissue, such as, for example, an endocardial wall. For example, the signal generator (122) may be a voltage pulse waveform generator and deliver a pulse waveform to the ablation device (110). The processor (124) may incorporate data received from memory (126), cardiac stimulator (128), and pacing device (130) to determine the parameters (e.g., amplitude, width, duty cycle, etc.) of the pulse waveform to be generated by the signal generator (122). The memory (126) may further store instructions to cause the signal generator (122) to execute modules, processes and/or functions associated with the system (100), such as pulse waveform generation and/or cardiac pacing synchronization. For example, the memory (126) may be configured to store pulse waveform and/or heart pacing data for pulse waveform generation and/or cardiac pacing, respectively.

In some embodiments, the ablation device (110) may include a catheter configured to receive and/or deliver the pulse waveforms described in more detail below. For example, the ablation device (110) may be introduced into an endocardial space of a chamber of the heart and positioned such that one or more electrodes (112) of the ablation device (110) is near target tissue (e.g., an endocardial wall). The ablation device (110) can then deliver the pulse waveforms to ablate tissue. The one or more electrodes (112) of the ablation device (110) may, in some embodiments, include one or more independently addressable electrodes, as further described with reference to FIGS. 4-8 below. Each electrode (112) may include an insulated electrical lead configured to sustain a voltage potential of at least about 500 V without dielectric breakdown of its corresponding insulation. In some embodiments, the insulation on each of the electrical leads may sustain an electrical potential difference of between about 200 V to about 3,000 V across its thickness without dielectric breakdown.

In some embodiments, the apparatus (120) can be coupled to a pacing device (130). The pacing device (130) may be suitably coupled to the patient (not shown) and configured to receive a heart pacing signal, e.g., generated by an optional cardiac stimulator (128) of the apparatus (120), for cardiac stimulation. An indication of the pacing signal may be transmitted by the cardiac stimulator (128) to the signal generator (122). Based on the pacing signal, an indication of a voltage pulse waveform may be selected, computed, and/or otherwise identified by the processor (124) and generated by the signal generator (122). In some embodiments, the signal generator (122) is configured to generate the pulse waveform in synchronization with the indication of the pacing signal (e.g., within a refractory window associated with an atrial or ventricular pacing signal). For example, in some embodiments, the refractory window may start substantially immediately following a ventricular pacing signal (or after a very small delay) and last for a duration of approximately 250 ms or less thereafter. In such embodiments, an entire pulse waveform may be delivered within this duration.

In some embodiments, the system (100) can include a tracking system or device (140). The tracking system (140) can be operatively coupled to the apparatus (120) and/or integrated into the apparatus (120). The tracking system (140) can enable impedance-based tracking and/or electromagnetic tracking of the ablation device (110), and in particular, a distal portion of the ablation device (110) as the ablation device (110) is navigated through anatomy. The tracking system (140) can include a field generator (142), including a set of transmitters configured to generate a field, e.g., a magnetic and/or electric field. For example, the field generator (142) can include a set of electrode patches that, between them, can generate and maintain electric potential differences over a range of frequencies. Alternatively or additionally, the field generator (142) can include a set of transmitter coils configured to generate a time-varying magnetic field. The generated electric and/or magnetic fields can be received as signals (e.g., voltages, currents, or both) by a set of sensor(s) (114) disposed near and/or incorporated into the ablation device (110). In an embodiment, the sensor(s) (114) can be electromagnetic sensors that are incorporated into a distal portion of the ablation device (110), e.g., a distal portion of a catheter. With tracked location information, a visual representation of the ablation device (100) can be displayed in an electroanatomical or anatomical map, e.g., to provide spatial context for visualizing catheter location. Such visual representations can be generated by, for example, processor (124) or another processing device coupled to and/or integrated into the apparatus (120) and/or tracking system (140). Suitable examples of tracking systems as used with ablation devices are described in U.S. patent application Ser. No. 16/785,392, filed Feb. 7, 2020, titled "METHODS, SYSTEMS, AND APPARATUSES FOR TRACKING ABLATION DEVICES AND GENERATING LESION LINES," the contents of which are incorporated by reference herein.

Optionally, the ablation device (110) can include an actuation mechanism (129), e.g., a knob, a lever, or other suitable mechanism for deflecting, steering, etc. the ablation device (110) in the anatomy. The actuation mechanism can be controlled by an operator based on a location of the distal portion of the ablation device (110). For example, based on the tracked location of the ablation device (110) as tracked by the tracking system (140), an operator can control an angle or orientation of the distal portion of the ablation device (110), so as to steer the ablation device (110) to a particular location.

The processor (124) may be any suitable processing device configured to run and/or execute a set of instructions or code. The processor may be, for example, a general purpose processor, a Field Programmable Gate Array (FPGA), an Application Specific Integrated Circuit (ASIC), a Digital Signal Processor (DSP), and/or the like. The processor may be configured to run and/or execute application processes and/or other modules, processes and/or functions associated with the system and/or a network associated therewith (not shown). The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

The memory (126) may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory (126) may store instructions to cause the processor (124) to execute modules, processes and/or functions associated with the system (100), such as pulse waveform generation and/or cardiac pacing.

The system (100) may be in communication with other devices (not shown) via, for example, one or more networks, each of which may be any type of network. A wireless network may refer to any type of digital network that is not connected by cables of any kind. However, a wireless network may connect to a wireline network in order to interface with the Internet, other carrier voice and data networks, business networks, and personal networks. A wireline network is typically carried over copper twisted pair, coaxial cable or fiber optic cables. There are many different types of wireline networks including, wide area networks (WAN), metropolitan area networks (MAN), local area networks (LAN), campus area networks (CAN), global area networks (GAN), like the Internet, and virtual private networks (VPN). Hereinafter, network refers to any combination of combined wireless, wireline, public and private data networks that are typically interconnected through the Internet, to provide a unified networking and information access solution.

Figure 2:
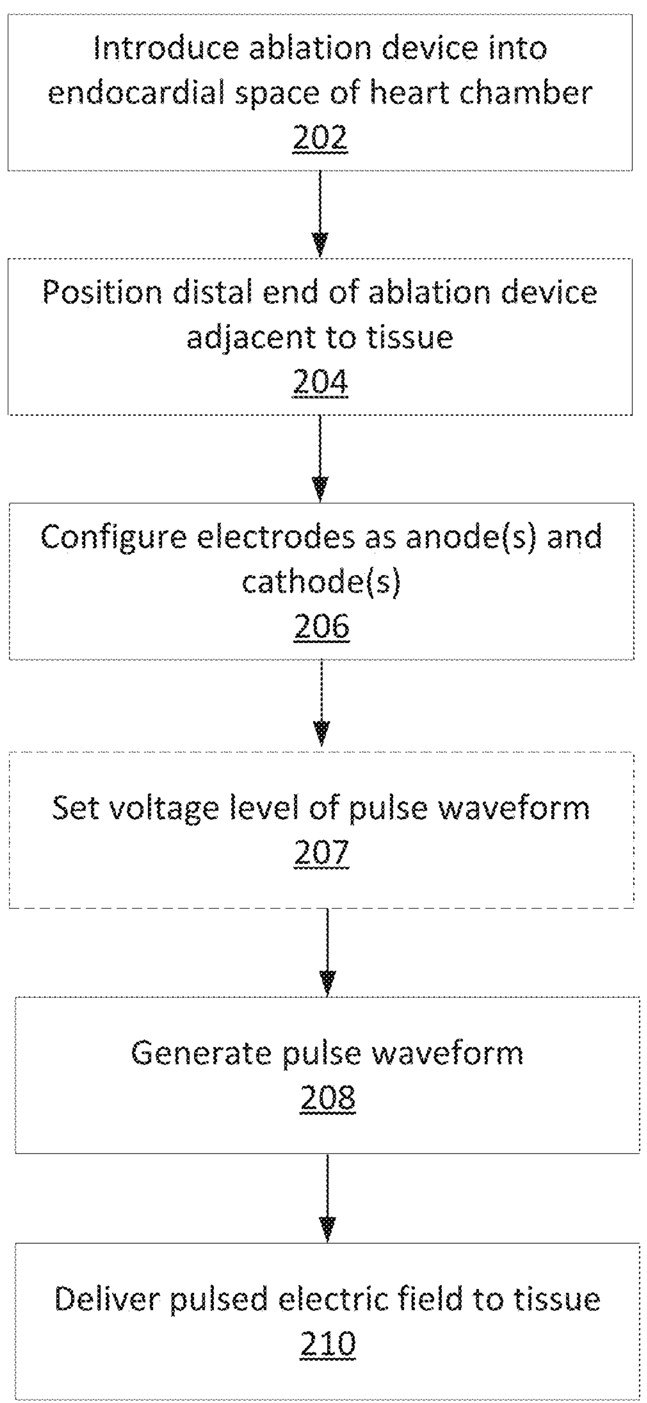
FIG. 2 illustrates a method for tissue ablation, according to embodiments.
Figure 3:
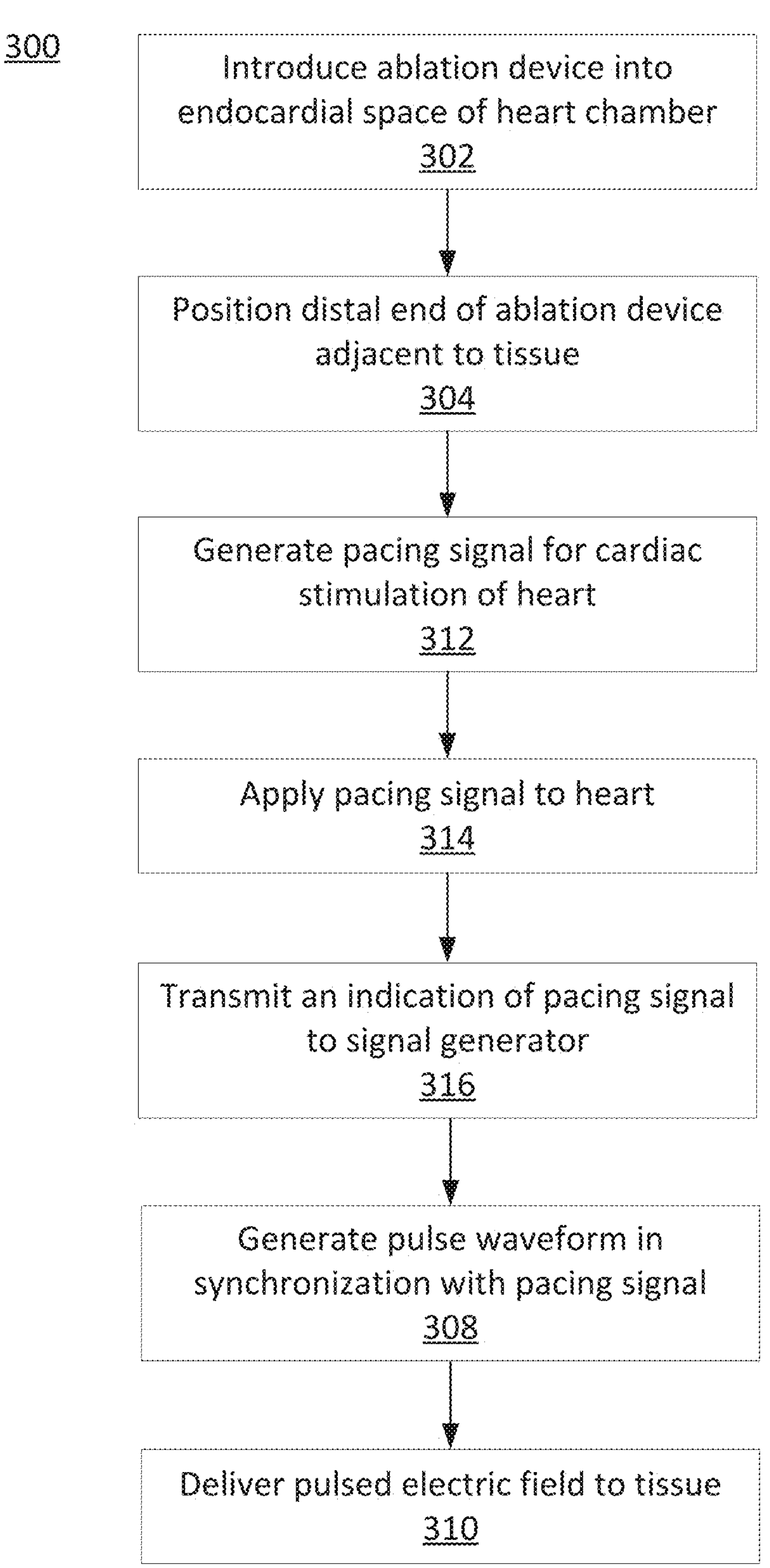
FIG. 3 illustrates a method for tissue ablation, according to embodiments.

Ablation systems described herein, e.g., system (100) depicted in FIG. 1, can be used according to methods, as depicted in FIGS. 2 and 3. In some embodiments, the ablation systems can be used to ablate tissue in a heart chamber, e.g., a left atrial chamber. Generally, the methods described here include introducing and disposing a device adjacent to and/or in contact with an endocardial wall. A pulse waveform may be delivered by one or more electrodes of the device to ablate tissue. In some embodiments, a cardiac pacing signal may synchronize the delivered pulse waveforms with the cardiac cycle. The tissue ablation thus performed may be delivered in synchrony with paced heartbeats and with less energy delivery to reduce damage to healthy tissue. It should be appreciated that any of the ablation devices described herein may be used to ablate tissue using the methods discussed below as appropriate.

In some embodiments, the ablation devices described herein may be used for focal ablation of cardiac features/structures identified to cause arrhythmia. Focal ablation may, for example, create a spot lesion that neutralizes a rotor while sparing surrounding tissue. Further detail of ablation zones generated using systems, devices, and methods disclosed herein are described with reference to FIGS. 5-8 below.

FIG. 2 depicts an example method (200) of ablating tissue. The method (200) includes the introduction of a device (e.g., ablation device (110)) into an endocardial space of a chamber of a heart, at (202). The device may be advanced to be disposed adjacent to tissue, at (204). The ablation device may include electrodes (e.g., electrodes (112)) that are positioned adjacent to the tissue. For example, the ablation device may be a linear flexible device that includes a plurality of distally placed electrodes, and such electrodes can be positioned near or in contact with a tissue surface, such as for example an endocardial wall in a cardiac chamber such as the left atrium or right atrium. The method (200) can include either manually or automatically configuring one or more electrodes of the ablation device as anode(s) and/or cathode(s), at (206). In some embodiments, the ablation device can include one or more distal electrode(s) and one or more proximal electrode(s), and at least one distal electrode and at least one proximal electrode can be configured as an anode-cathode set. For example, as further described below with reference to FIGS. 4-10, an ablation device can include a distal tip electrode and two proximal electrodes, and the distal tip electrode can be paired with the two proximal electrodes to form an anode-cathode set. In alternate embodiments, the ablation device can have fewer than or more than three electrodes, for example two, four, five or six electrodes, with the electrodes comprising distal and proximal electrode subsets. In some embodiments, voltage pulse waveforms may be selectively delivered to an electrode set such as an anode-cathode set for ablation of tissue. For example, a distal tip electrode of an ablation device may be selected as an anode, while proximal electrodes of the ablation device may be selected as cathodes, with the voltage pulse waveform applied between the anode and cathodes.

Optionally, a voltage level of the pulse waveform or a portion of the pulse waveform (e.g., an amplitude of one or more voltage pulses) can be set, at (207). For example, the voltage level can be increased to produce deeper ablation zones, which can be useful when tissue is thicker. As a set of non-limiting examples, the amplitude of individual pulses of an example pulse waveform can be in the range from about 400 V, about 1,000 V, about 5,000 V, about 10,000 V, about 15,000 V, including all values and sub ranges in between.

A pulse waveform may be generated by a signal generator (e.g., the signal generator (122)), at (208). In some embodiments, the pulse waveform may be a voltage pulse waveform including a plurality of levels of a hierarchy, while in alternate embodiments other waveform implementations can be employed. Examples of suitable pulse waveforms including a plurality of levels of a hierarchy are disclosed in International Application Serial No. PCT/US2016/057664, filed on Oct. 19, 2016, titled “SYSTEMS, APPARATUSES AND METHODS FOR DELIVERY OF ABLATIVE ENERGY TO TISSUE,” and International Application Serial No. PCT/US2019/031135, filed May 7, 2019, titled “SYSTEMS, APPARATUSES AND METHODS FOR DELIVERY OF ABLATIVE ENERGY TO TISSUE,” the contents of each of which are hereby incorporated by reference in their entirety. A variety of hierarchical waveforms may be generated with a signal generator (e.g., signal generator (122)) as disclosed herein.

The generated pulse waveform may be delivered to the anode-cathode electrode set(s) such that the electrode set(s) generate an electric field that ablates the tissue, at (210). For example, a distal tip electrode of an ablation catheter can be polarized with a first electrical polarity and proximal electrodes of the ablation catheter can be polarized with a second electrical polarity opposite the first electrical polarity, such that the distal tip electrode and the proximal electrodes generate an electric field that is capable of forming lesions. As another example, in an embodiment with four electrodes, a distal pair of electrodes can have one electrical polarity while a proximal pair of electrodes can have an opposite electrical polarity during ablation delivery, with the plurality of electrodes thus collectively generating an electric field for ablation. Further details of such embodiments are described with reference to FIGS. 4-10. The spatial form of the lesion can have a controlled depth or volume, e.g., through the application of suitable waveforms, as described herein, and with appropriate voltage levels, electrode geometry, and/or electrode pairing. In some embodiments, one or more voltage pulse waveform(s) may be applied over a series of heartbeats, e.g., during refractory time windows, as further described below.

In some embodiments, the voltage pulse waveforms described herein may be applied during a refractory period of the cardiac cycle so as to avoid disruption of the sinus rhythm of the heart. FIG. 3 depicts another example method (300) of ablating tissue. The method (300) can be similar to the method (200), described above, but include steps for applying a pulse waveform in synchrony with one or more pacing signals. The method (300) includes introduction of a device (e.g., ablation device (110)) into an endocardial space of a chamber of a heart, at (302). The device may be advanced to be disposed adjacent to a tissue wall of the heart, e.g., at an endocardial surface in the left or right atrium. For example, the ablation device may be a linear flexible device that includes a plurality of distally placed electrodes, and such electrodes can be positioned near or in contact with an endocardial wall. In some embodiments, a pacing signal may be generated for cardiac stimulation of the heart, at (312). The pacing signal may then be applied to the heart, at (314). For example, the heart may be electrically paced with a cardiac stimulator (e.g., cardiac stimulator (128)) to ensure pacing capture to establish periodicity and predictability of the cardiac cycle. One or more of atrial and ventricular pacing may be applied. An indication of the pacing signal may be transmitted to a signal generator, at (316). A time window within the refractory period of the cardiac cycle may then be defined within which one or more voltage pulse waveforms may be delivered. In some embodiments, a refractory time window may follow a pacing signal. For example, a common refractory time window may lie between both atrial and ventricular refractory time windows.

A pulse waveform may be generated in synchronization with the pacing signal, at (308). For example, a voltage pulse waveform may be applied in the common refractory time window. In some embodiments, the pulse waveform may be generated with a time offset with respect to the indication of the pacing signal. For example, the start of a refractory time window may be offset from the pacing signal by a time offset. The voltage pulse waveform(s) may be applied over a series of heartbeats over corresponding common refractory time windows. The generated pulse waveform may be delivered to the ablation device such that the ablation device generates a pulsed electric field for ablating the tissue, at (310).

Figure 4:
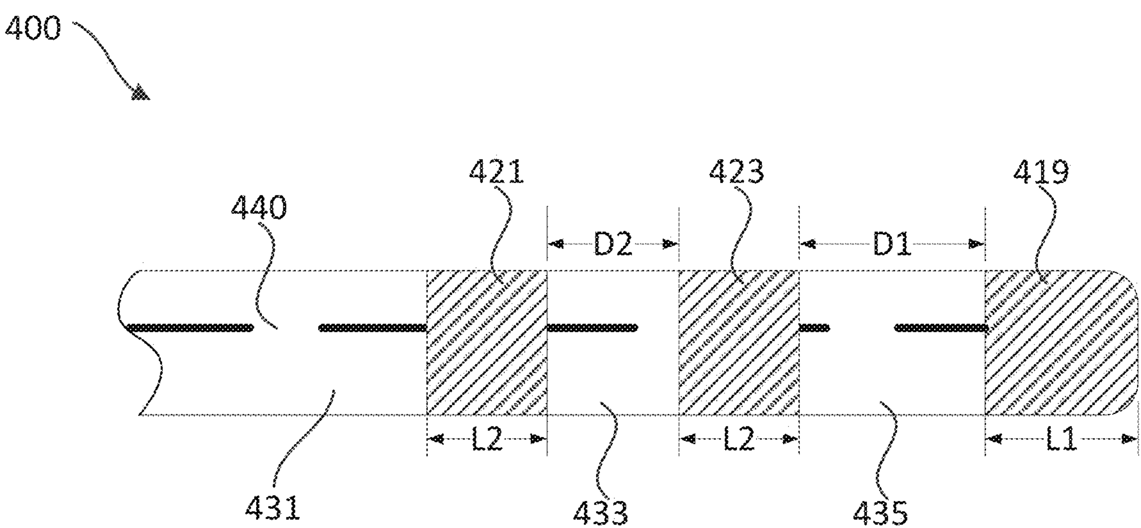
FIG. 4 illustrates a schematic view of a distal end of an ablation catheter, according to embodiments.

The methods described herein can be implemented using systems including one or more multi-electrode ablation devices. FIG. 4 is a side view of an ablation device (400). The ablation device (400) can include components that are structurally and/or functionally similar to the ablation device (110), as described above with reference to FIG. 1. The ablation device (400) can be a flexible linear catheter with a multiplicity of distally placed electrodes. The ablation device (400) can include a shaft or body (431) and a plurality of electrodes (419, 421, 423) including a distal tip electrode (419) and proximal electrodes (421, 423). The plurality of electrodes (419, 421, 423) can be located on a distal portion of the body (431), with the proximal electrodes (421, 423) located proximal to the tip electrode (419), and each electrode (419, 421, 423) being separated from adjacent electrodes by shaft portions (433, 435).

The electrodes (419, 421, 423) can be positioned such that they are adjacent to and/or in contact with tissue, e.g., endocardial tissue. But although the electrodes (419, 421, 423) may be disposed to touch endocardial tissue, it should be appreciated that the electrodes (419, 421, 423) need not contact the endocardial tissue to form ablation zones, as described herein.

One or more of the electrodes (419, 421, 423) can be independently addressable electrodes. In some embodiments, subsets of the electrodes (419, 421, 423) may be jointly wired. For example, the proximal electrodes (421, 423) may be jointly wired, while the distal tip electrode (419) may be independently addressable or wired separately from the proximal electrodes (421, 423). One of more of the electrodes (419, 421, 423) may be coupled to an insulated electrical lead configured to sustain a voltage potential of at least about 500 V without dielectric breakdown of its corresponding insulation. In other embodiments, the insulation on each of the electrical leads may sustain an electrical potential difference of between about 200 V to about 2000 V across its thickness, including all subranges and values in between, without dielectric breakdown. The body (431) may include the insulated electrical leads of each electrode (419, 421, 423), e.g., within an inner defined lumen.

In some embodiments, the shaft portions (433, 435) separating the electrodes (419, 421, 423) can be flexible such that the ablation device (400) can be deflected, e.g., to be positioned adjacent to target tissue (e.g., soft tissue within the heart). In other embodiments one or both of the intermediate shaft portions (433, 435) can be rigid or semi-rigid. A pull wire (440) can be disposed within the ablation device (400) for deflecting the ablation device (400). The pull wire (440) can be attached to a rigid portion of the body (431), e.g., where the electrodes (419, 421, 423) are disposed, and pulled on to deflect portions of the body (431) proximal to the attachment location. In some embodiments, the shaft portions (433, 435) are configured to deflect along with more proximal portions of the body (440). The pull wire (440) can be attached to a handle (not depicted) located at a proximal end of the ablation device (400), which can be used to control the deflection of the body (431). The handle can include a mechanism for deflecting or steering the distal portion of the ablation device (400), e.g., via tensioning of the pull wire (440).

According to methods described herein, the ablation device (400) can be used to generate an ablation zone in tissue through the application of high voltage waveforms for pulsed electric field ablation, whereby a zone of ablated tissue is generated via irreversible electroporation. The ablation device (400) can be used in clinical applications, including, for example, in cardiac ablation for the treatment of cardiac arrhythmias. In some embodiments, the ablation device (400) can generate focal or localized ablation zones that can be about 5 mm to about 15 mm in diameter and about 1 mm to about 6 mm in depth.

In some embodiments, one or more pulse waveforms may be applied between the electrodes (419, 421, 423) configured in anode and cathode sets. For example, distal tip electrode (419) can be electrically paired with proximal electrodes (421, 423). A signal generator (e.g., signal generator (122)) can be used to deliver a pulsed waveform to the electrodes (419, 421, 423) such that the tip electrode (419) is polarized with a first electrical polarity and the two proximal electrodes (421, 423) are jointly polarized with a second electrical polarity opposite to the first electrical polarity. In some embodiments, the pulse waveform can be a hierarchical waveform, as described above, while in other embodiments, other waveform structures can be employed. When the electrodes (419, 421, 423) are paired as such, and energized with a voltage pulse waveform of suitable amplitude, the electrodes (419, 421, 423) can generate an ablation zone having a depth that is generally independent of an orientation of the electrodes (419, 421, 423) relative to the tissue, as further described below with reference to FIGS. 5-8.

In some embodiments, the body (431) can have a diameter of between about 1 mm and about 5 mm, including all subranges and values in between. For example, in some embodiments, the body (431) can have a diameter of between about 4 French (1.33 mm) and about 15 French (5 mm). In some embodiments, the distal tip electrode (419) can have a length L1 in a range from about 1 mm to about 8 mm. In some embodiments, the proximal electrodes (421, 423) can each have a length L2 in a range from about 1 mm to about 6 mm. In some embodiments, the distal tip electrode (419) can have a length L1 that is greater than a length L2 of the proximal electrodes (421, 423). In some embodiments, the proximal electrodes (421, 423) can have varying lengths. In some embodiments, the shaft portions (433, 435) that separate adjacent electrodes (419, 421, 423) can each have a length in a range between about 1 mm to about 10 mm. In some embodiments, a distance D1 separating tip electrode (419) from a first proximal electrode (423) may be greater than a distance D2 separating the first proximal electrode (423) from a second proximal electrode (421). Alternatively, the distance D1 and the distance D2 separating adjacent electrodes (419, 421, 423) can be equal to one another, or the distance D2 can be greater than the distance D1.

While ablation device (400) is depicted with a single distal tip electrode (419) and two proximal electrodes (421, 423), it can be appreciated that ablation device (400) can include additional numbers of distal electrode(s) and/or proximal electrode(s). For example, in an alternative arrangement, ablation device (400) can include more than two proximal electrodes, and a subset of the proximal electrodes (e.g., two of the proximal electrodes) can be selected to generate a pulsed electric field.

Figure 9:
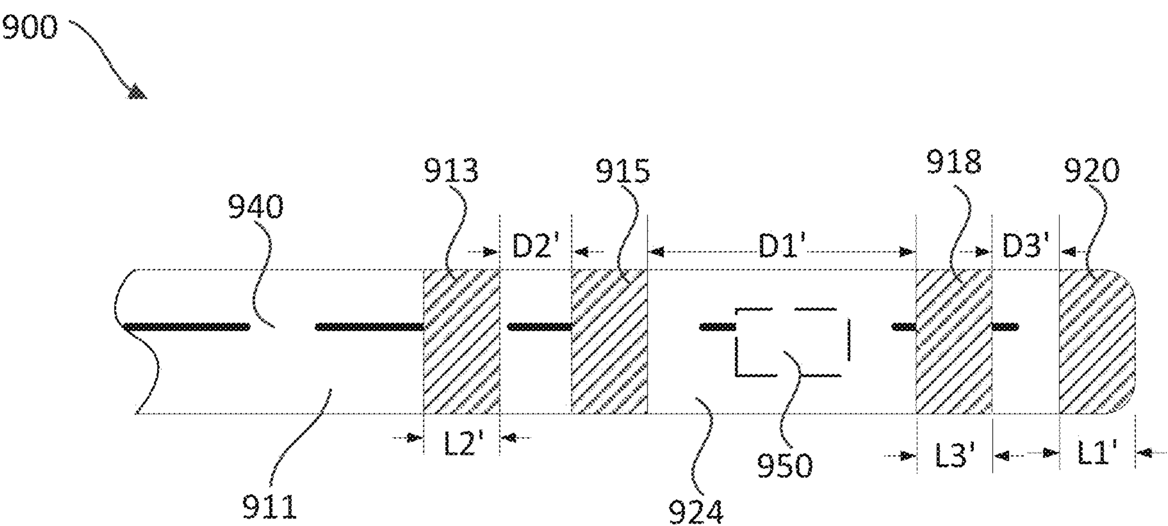
FIG. 9 illustrates a schematic view of a distal end of an ablation catheter, according to embodiments.

FIG. 9 schematically depicts a distal portion of an ablation device (900). The ablation device (900) can be and/or include components that are structurally and/or functionally similar to other ablation devices described herein, including, for example, the ablation device (110), as described above with reference to FIG. 1. The ablation device (900) can be a flexible linear catheter with a distal portion (911) including a set of distal electrodes (918, 920) and a set of proximal electrodes (913, 915). The set of distal electrodes (918, 920) can be separated from the set of proximal electrodes (913, 915) by a shaft portion (924). In some embodiments, the shaft portion (924) can be flexible, while in alternative embodiments, the shaft portion (924) can be rigid or substantially rigid. A pull wire (940) can be disposed within the ablation device (900) for deflecting the ablation device (900). The pull wire (940) can be coupled within the shaft of the ablation device (900) to an internal location, e.g., between the proximal electrode (913) and the distal electrode (920). For example, the pull wire (940) can be attached proximal to the proximal electrode (913), proximal to the distal electrode (918), between the distal electrodes (918, 920), etc. In some embodiments, the pull wire (940) can be coupled to a handle mechanism or actuator (not shown) with which a user can manipulate an actuation element (e.g., a rocker, a knob, a lever, or other suitable mechanism) to deflect the distal portion (911) of the ablation device (900). Depending on the location where the pull wire (940) is coupled to the shaft (e.g., distal or proximal to the shaft portion (924)), and on the flexibility of the shaft portion (924), the shaft portion (924) can deflect or not when a portion of the shaft is deflected using the pull wire (940).

In some embodiments, one or more of the electrodes (913, 915, 918, 920) can be independently addressable electrodes, with individual insulated wires or leads coupling to each independently addressable electrode. In some embodiments, subsets of the electrodes (913, 915, 918, 920) can be jointly wired. For example, the proximal electrodes (913, 915) can be jointly wired using a single lead, and the distal electrodes (918, 920) can be jointly wired using a single lead. Alternatively, the distal tip electrode (920) can be independently addressable and wired with its own lead, the distal electrode (918) can be wired with its own lead, and the proximal electrodes (913, 915) can be jointly wired with a single lead. The insulation covering each lead can have sufficient dielectric strength to withstand a potential difference of between about 200 V to about 2000 V across its thickness, including all subranges and values in between, without dielectric breakdown. In an embodiment, the insulation covering each lead can have sufficient dielectric strength to withstand a potential difference of at least about 700 V without dielectric breakdown.

Optionally, a sensor (950) can be incorporated into the distal portion (911) of the catheter, with one or more separate leads (not shown) attached to the sensor (950). The sensor (950) can be used, for example, to enable tracking of location, orientation, etc. of the ablation device (900) in an anatomy (e.g., a cardiac chamber). For example, the sensor (950) can be an electromagnetic sensor that can receive electromagnetic signals from transmitter coils associated with a location tracking system (e.g., tracking system (140)). The transmitter coils can be configured to generate a time-varying field that is received as signals (e.g., voltages, currents, or both) by the sensor (950). In some embodiments, one or more electrodes (913, 915, 918, 920) or another electrode (not depicted) can be used to receive electrocardiogram (ECG) data, which can provide diagnostic information or be used to assess location. For example, the distal electrodes (918, 920) can be used to collect ECG data, which can be displayed as a bipolar (differential) signal on a display associated with an ECG system. Additionally or alternatively, electrodes (913, 915, 918, 920) can be used to sense signals from an impedance localization system for tracking the ablation device (900). With tracked location information, a visual representation of the ablation device (900) can be displayed in an electroanatomical or anatomical map, e.g., to provide spatial context for visualizing catheter location.

According to methods described herein, the ablation device (900) can be used to generate an ablation zone in tissue through the application of high voltage waveforms for pulsed electric field ablation, whereby a zone of ablated tissue is generated via irreversible electroporation. The ablation device (900) can be operatively coupled to a signal generator (e.g., signal generator (122)), which can be used to deliver irreversible electroporation ablation to a tissue site. The signal generator can generate one or more pulse waveforms that are applied between the electrodes (913, 915, 918, 920) configured as anode and cathode sets. For example, the set of distal electrodes (918, 920) and the set of proximal electrodes (913, 915) can be paired as an anode-cathode pair to generate a lesion via irreversible electroporation. Stated differently, the set of distal electrodes (918, 920) can be activated with a first polarity and the set of proximal electrodes (913, 915) can be activated with a second polarity opposite the first polarity, such that the electrodes (913, 915, 918, 920) collectively generate an electric field that ablates the tissue site. When the electrodes (913, 915, 918, 920) are paired as such, and energized with an appropriate voltage pulse waveform of suitable amplitude, the electrodes (913, 915, 918, 920) can generate an ablation zone having a depth that is generally independent of an orientation of the electrodes (913, 915, 918, 920) relative to the tissue, as further described below with reference to FIGS. 5-8. Such a pairing scheme is capable of generating lesions having a depth that is generally independent of catheter orientation.

In some embodiments, the shaft of the ablation device (900) can have a diameter of between about 4 French (1.33 mm) and about 15 French (5 mm). In some embodiments, each distal electrode (918, 920) can have the same length, e.g., a length L1', and each proximal electrode (913, 915) can have the same length, e.g., a length L2'. In other embodiments, the lengths of at least some of the distal electrodes can be different from each other, or the lengths of at least some of the proximal electrodes can be different from each other. The length L1' of each distal electrode (918, 920) can be substantially equal to, greater than, or less than the length L2' of each proximal electrode. In some embodiments, each distal electrode (918, 920) can have different lengths and/or each proximal electrode (913, 915) can have different lengths. In some embodiments, the combined length of the distal electrodes (918, 920) can be substantially equal to, greater than, or less than the combined length of the proximal electrodes (913, 915). The proximal electrodes (913, 915) can be separated from each other by a distance D2', and the distal electrodes (918, 920) can be separated from each other by a distance D3'. In some embodiments, the distance D2' separating the proximal electrodes (913, 915) can be substantially equal to, greater than, or less than the distance D3' separating distal electrodes (918, 920). In some embodiments, the distances D2' and D3' can be less than a distance D1' separating the distal electrode (918) from the proximal electrode (915). The distances D1', D2' and D3' can generally lie in the range between 0.5 mm and 12 mm. In some embodiments, the ratio D2'/D1' can lie in the range between 1 and 20.

Figure 10:
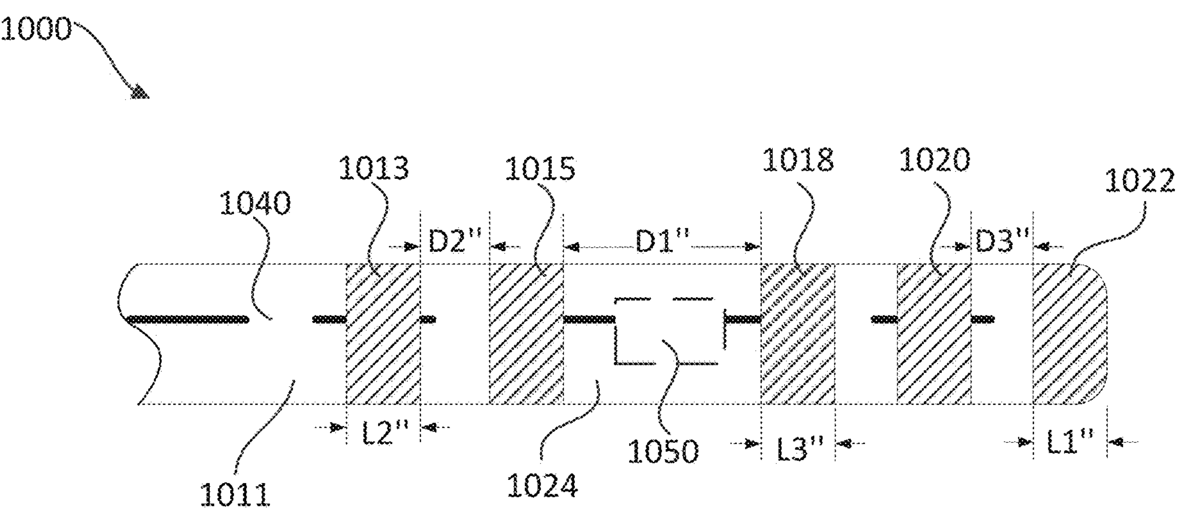
FIG. 10 illustrates a schematic view of a distal end of an ablation catheter, according to embodiments.

FIG. 10 schematically depicts a distal portion of an ablation device (1000). The ablation device (1000) can be and/or include components that are structurally and/or functionally similar to other ablation devices described herein. The ablation device (1000) can be a flexible linear catheter with a distal portion (1011) including a set of distal electrodes (1018, 1020, 1022) and a set of proximal electrodes (1013, 1015). The set of distal electrodes (1018, 1020, 1022) can be separated from the set of proximal electrodes (1013, 1015) by a shaft portion (1024). In some embodiments, the shaft portion (1024) can be flexible, while in alternative embodiments, the shaft portion (1024) can be rigid or substantially rigid. A pull wire (1040) can be disposed within the ablation device (1000) for deflecting the ablation device (1000). The pull wire (1040) can be coupled within the shaft of the ablation device (1000) to an internal location, e.g., between the proximal electrode (1013) and the distal electrode (1022). For example, the pull wire (1040) can be attached proximal to the proximal electrode (1013), proximal to the distal electrode (1018), between the distal electrodes (1018, 1022), etc. In some embodiments, the pull wire (1040) can be coupled to a handle mechanism or actuator (not shown) with which a user can manipulate an actuation element (e.g., a rocker, a knob, a lever, or other suitable mechanism) to deflect the distal portion (1011) of the ablation device (1000). Depending on the location that the pull wire (1040) is coupled to the shaft (e.g., distal or proximal to the shaft portion (1024)), and on the flexibility of the shaft portion (1024), the shaft portion (1024) can deflect or not when a portion of the shaft is deflected using the pull wire (1040).

In some embodiments, one or more of the electrodes (1013, 1015, 1018, 1020, 1022) can be independently addressable electrodes, with individual insulated wires or leads coupling to each electrode. In some embodiments, subsets of the electrodes (1013, 1015, 1018, 1020, 1022) can be jointly wired. For example, the proximal electrodes (1013, 1015) can be jointly wired using a single lead, and the distal electrodes (1018, 1020, 1022) can be joined wired using a single lead. Alternatively, the distal tip electrode (1022) can be independently addressable and wired with its own lead, the distal electrodes (1018, 1020) can be jointly wired with a single lead, and the proximal electrodes (1013, 1015) can be jointly wired with a single lead. The insulation covering each lead can have sufficient dielectric strength to withstand a potential difference of between about 200 V to about 2000 V across its thickness, including all subranges and values in between, without dielectric breakdown. In an embodiment, the insulation covering each lead can have sufficient dielectric strength to withstand a potential difference of at least about 700 V without dielectric breakdown.

Optionally, a sensor (1050) can be incorporated into the distal portion (1011) of the catheter, with one or more separate leads (not shown) attached to the sensor (1050). The sensor (1050) can be used, for example, to enable tracking of location, orientation, etc. of the ablation device (1000) in an anatomy (e.g., a cardiac chamber). For example, the sensor (1050) can be an electromagnetic sensor that can receive electromagnetic signals from transmitter coils associated with a location tracking system (e.g., tracking system (140)). In some embodiments, one or more electrodes (1013, 1015, 1018, 1020, 1022) or another electrode (not depicted) can be used to receive ECG data, which can provide diagnostic information or be used to assess location. For example, the distal electrodes (1018, 1020) can be used to collect ECG data, which can be displayed as a bipolar (differential) signal on a display associated with an ECG system. Additionally or alternatively, electrodes (1013, 1015, 1018, 1020, 1022) can be used to sense signals from an impedance localization system for tracking the ablation device (1000). With tracked location information, a visual representation of the ablation device (1000) can be displayed in an electroanatomical or anatomical map, e.g., to provide spatial context for visualizing catheter location.

According to methods described herein, the ablation device (1000) can be used to generate an ablation zone in tissue through the application of high voltage waveforms for pulsed electric field ablation, whereby a zone of ablated tissue is generated via irreversible electroporation. The ablation device (1000) can be operatively coupled to a signal generator (e.g., signal generator (122)), which can be used to deliver irreversible electroporation ablation to a tissue site. The signal generator can generate one or more pulse waveforms that are applied between the electrodes (1013, 1015, 1018, 1020, 1022) configured as anode and cathode sets. For example, the set of distal electrodes (1018, 1020, 1022) and the set of proximal electrodes (1013, 1015) can be paired as an anode-cathode pair to generate a lesion via irreversible electroporation. When the electrodes (1013, 1015, 1018, 1020, 1022) are paired as such, and energized with an appropriate voltage pulse waveform of suitable amplitude, the electrodes (1013, 1015, 1018, 1020, 1022) can generate an ablation zone having a depth that is generally independent of an orientation of the electrodes (1013, 1015, 1018, 1020, 1022) relative to the tissue, as further described below with reference to FIGS. 5-8.

Figure 5:
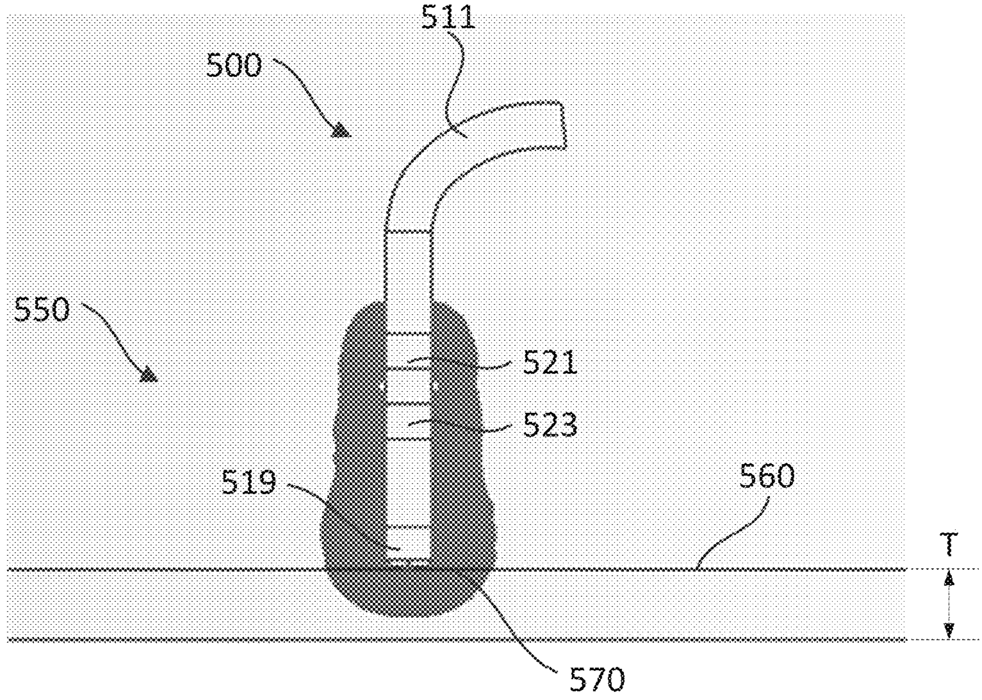
FIG. 5 illustrates an electric field generated by electrodes of an ablation catheter disposed near tissue, according to embodiments.

FIGS. 5-8 depict different ablation zones that can be generated in tissue using systems, devices, and methods, as described herein. FIG. 5 depicts a simulation of an ablation zone that can be generated in a tissue wall (560) with an ablation device (500). The ablation device (500) can be structurally and/or functionally similar to other ablation devices described herein, including, for example, ablation devices (110, 400, 900, 1000). For example, the ablation device (500) can include a body (511), a distal tip electrode (519), and proximal electrodes (521, 523).

As depicted in FIG. 5, the distal tip electrode (519) can be apposed approximately normal to a tissue wall 560 (e.g., a cardiac tissue wall). Stated differently, a distal portion of the body (511) of the ablation device (500), including at least the distal tip electrode (519) can be positioned to extend in a direction approximately normal to a surface of the tissue wall (560). The distal portion of the body (511) can be disposed generally in a blood pool (550) adjacent to the tissue wall (560), e.g., a blood pool within a cardiac chamber. The tissue wall (560) can have a thickness T in the range of approximately 1 mm to approximately 8 mm, including all values and subranges in between.

According to methods described herein, a pulse waveform can be generated, e.g., using a signal generator (e.g., signal generator (122)), and delivered to the ablation device (500). To form the simulated ablation zone (570) depicted in FIG. 5, the tip electrode (519) is configured to have a first polarity, and the proximal electrodes (521, 523) are configured to have a second polarity opposite the first polarity. For example, the signal generator can be configured to deliver output signals associated with the pulse waveform and having opposite polarities to the tip electrode (519) and the proximal electrodes (521, 523), respectively. As such, the tip electrode (519) can be polarized with one electrical polarity, and the proximal electrodes (521, 523) can be polarized with the opposite electrical polarity. The tip electrode (519) and the proximal electrodes (521, 523) can be polarized with a pulse waveform having a voltage amplitude of at least about 0.5 kV (e.g., 1 kV) to generate a pulsed electric field having the ablation zone (570).

Figure 6:
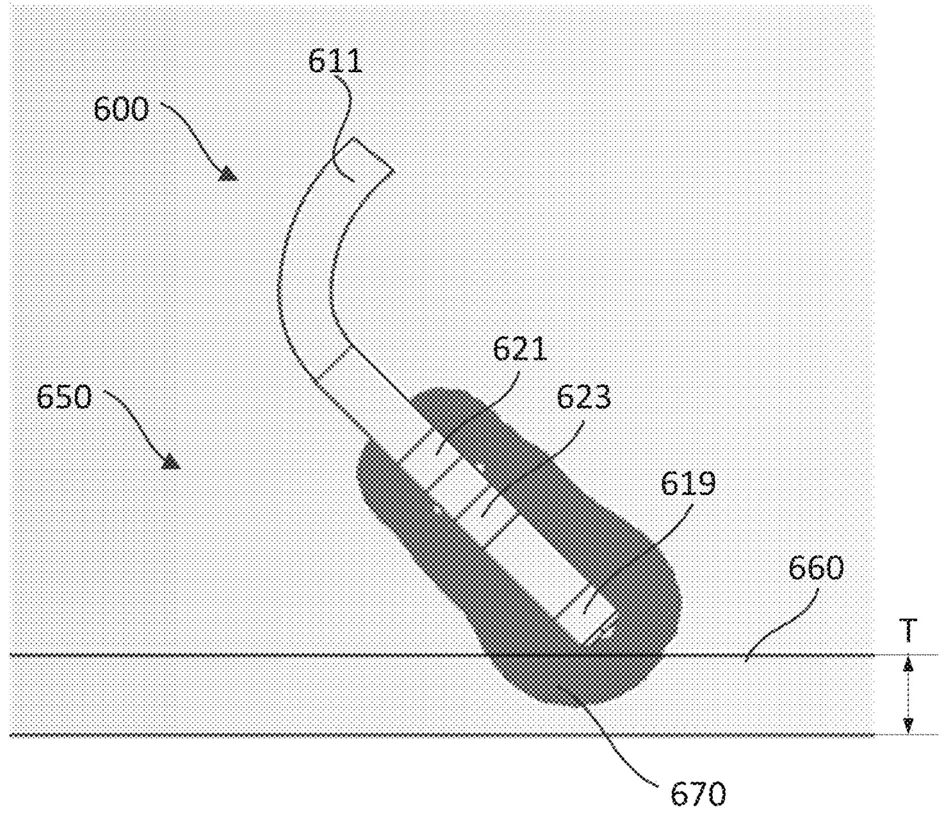
FIG. 6 illustrates an electric field generated by electrodes of an ablation catheter disposed near tissue, according to embodiments.

FIG. 6 depicts a simulation of an ablation zone generated in a tissue wall (660) with an ablation device (600) in an oblique orientation relative to the tissue wall (660). The ablation device (600) can be structurally and/or functionally similar to other ablation devices described herein, including, for example, ablation devices (110, 400, 500). For example, the ablation device (600) can include a body (611), a distal tip electrode (619), and proximal electrodes (621, 623).

As depicted in FIG. 6, the distal tip electrode (619) can be apposed at an angle (e.g., between about 0 and about 90 degrees, including all subranges and values in between) relative to the tissue wall (660). The distal portion of the ablation device (600) can be positioned in a blood pool (650). The tissue wall (660) can have a thickness T in the range of approximately 1 mm to approximately 8 mm. Using a pulse waveform having the same voltage amplitude (e.g., 1 kV), and the same electrode subset configuration (i.e., with the tip electrode (619) having one electrical polarity and proximal electrodes (621, 623) having the opposite electrical polarity), the electrodes (619, 621, 623) can generate a pulsed electric field having an ablation zone (670). In comparing the ablation zone (670) generated by the obliquely apposed ablation device (600) and the ablation zone (570) generated by the normally apposed ablation device (500), the depths of the ablated tissue zones are similar. Specifically, the ablation zone (670) generated by the obliquely apposed ablation device (600) has a depth that is approximately equal to the depth of the ablation zone (570) generated by the normally apposed ablation device (500). Accordingly, the ablation devices described herein (e.g., ablation devices (500, 600)) can generate ablation zones in a manner that is orientation-independent.

Figure 7:
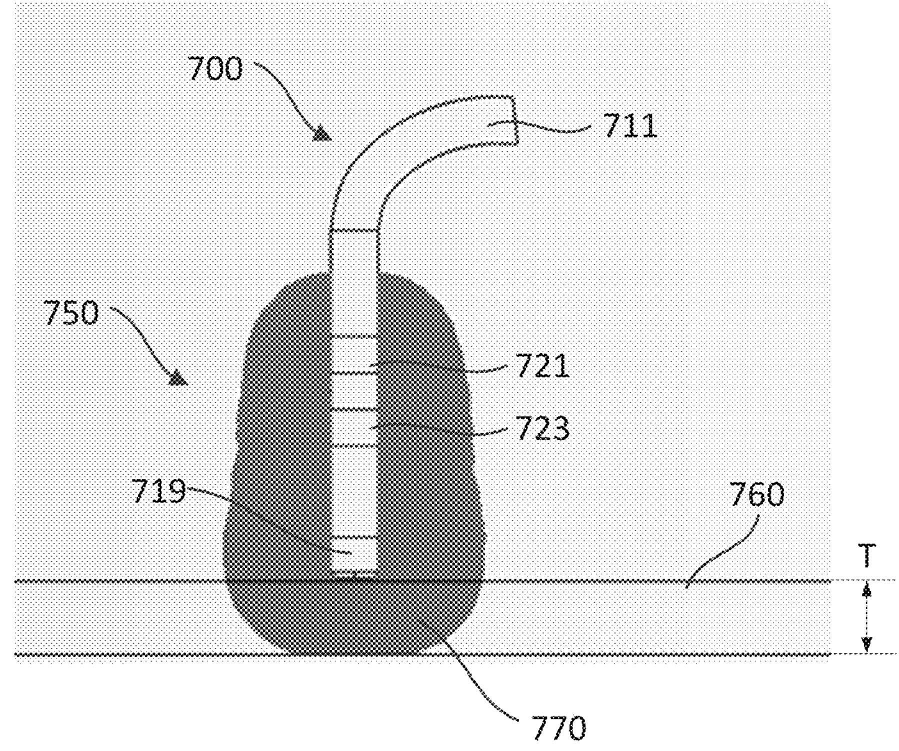
FIG. 7 illustrates an electric field generated by electrodes of an ablation catheter disposed near tissue, according to embodiments.
Figure 8:
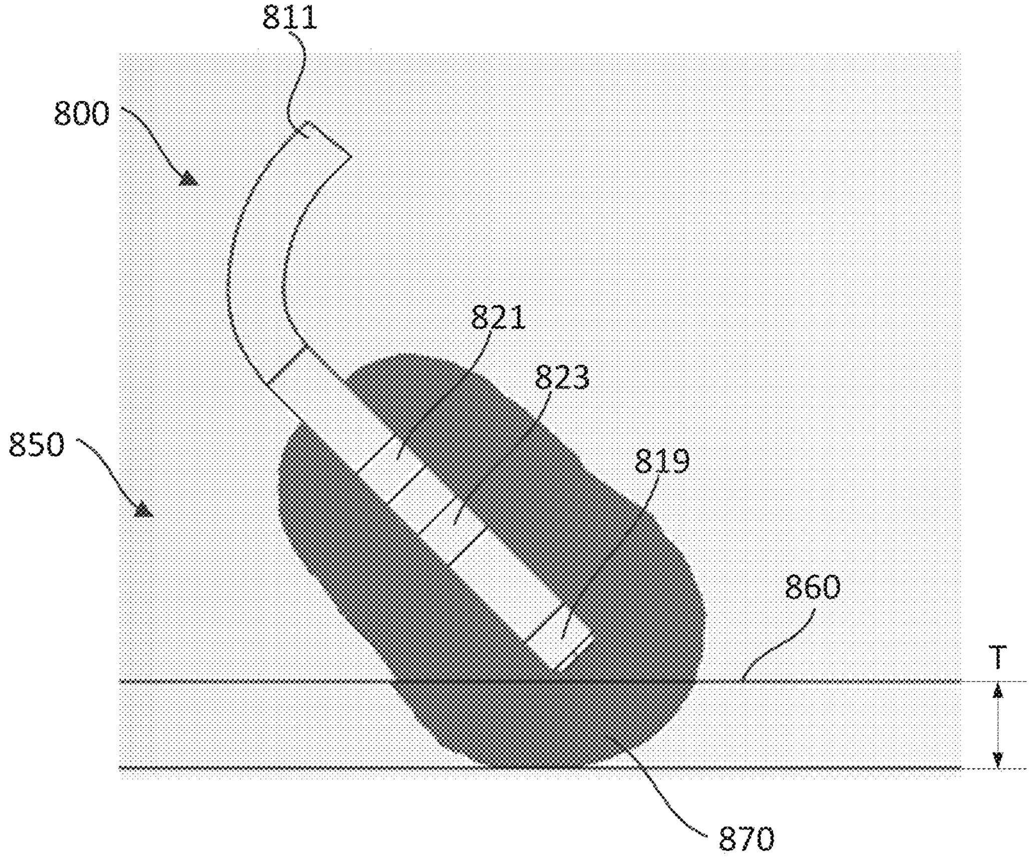
FIG. 8 illustrates an electric field generated by electrodes of an ablation catheter disposed near tissue, according to embodiments.

Devices and systems, as described here, can generate controllable ablation zones in an orientation-independent manner with pulse waveforms having a range of voltage amplitudes, e.g., amplitudes ranging from about 400 V, about 1,000 V, about 5,000 V, about 10,000 V, about 15,000 V, including all values and sub ranges in between. As an example, FIGS. 7 and 8 depict simulated ablation zones (770, 870) that are generated using pulse waveforms having a higher voltage than that of FIGS. 5 and 6. For example, the ablation devices (700, 800) depicted in FIGS. 7 and 8 can be energized with pulse waveforms having a voltage amplitude of 2 kV.

FIG. 7 depicts a simulated ablation zone (770) generated in a tissue wall (760) with an ablation device (700) that is apposed approximately normal to the tissue wall (760). The ablation device (700) can be structurally and/or functionally similar to other ablation devices described herein, including, for example, ablation devices (110, 400, 500, 600). For example, the ablation device (700) can include a body (711), a distal tip electrode (719), and proximal electrodes (721, 723).

As depicted in FIG. 7, the distal tip electrode (719) can be apposed approximately normal (e.g., about 90 degrees) relative to the tissue wall (760). The distal portion of the ablation device (700) can be positioned in a blood pool (750). The tissue wall (760) can have a thickness T in the range of approximately 1 mm to approximately 8 mm. Using a pulse waveform with individual pulses having an amplitude of 2 kV, and with the tip electrode (719) and proximal electrodes (721, 723) being oppositely polarized, the electrodes (719, 721, 723) can generate a pulsed electric field having an ablation zone (770). As shown, the ablation zone (770) can have a depth that is greater than the depth of the ablation zones (570, 670) due to the higher voltage of the pulse waveform.

FIG. 8 depicts a simulated ablation zone (870) generated in a tissue wall (860) with an ablation device (800) that is apposed obliquely relative to the tissue wall (860). The ablation device (800) can be structurally and/or functionally similar to other ablation devices described herein, including, for example, ablation devices (110, 400, 500, 600, 700). For example, the ablation device (800) can include a body (811), a distal tip electrode (819), and proximal electrodes (821, 823).

As depicted in FIG. 8, the distal tip electrode (819) can be apposed obliquely (e.g., between about 0 and about 90 degrees, including all subranges and values in between) relative to the tissue wall (860). The distal portion of the ablation device (800) can be positioned in a blood pool (850). The tissue wall (860) can have a thickness T in the range of approximately 1 mm to approximately 8 mm. Using a pulse waveform with individual pulses having an amplitude of 2 kV, and with the tip electrode (819) and proximal electrodes (821, 823) being oppositely polarized, the electrodes (819, 821, 823) can generate a pulsed electric field having an ablation zone (870). As shown, the ablation zone (870) can have a depth that is greater than the depth of the ablation zones (570, 670) due to the higher voltage of the pulse waveform. When compared to the ablation zone (770) of FIG. 7, the ablation zone (870) has a similar depth (e.g., depth that is approximately the same). Accordingly, FIGS. 7 and 8 provide a further example of the ablation devices described herein being capable of generating controllable ablation zones that are independent of an orientation of the ablation device relative to the tissue wall.

It should be appreciated that the tip of the ablation catheter of the present invention can be apposed at a tissue surface with any orientation that is convenient in the clinical application, whether normal, oblique or tangential to the local tissue surface. The specific examples provided herein are given for illustrative purposes only.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

As used herein, the terms "set" and/or "subset" of components (e.g., electrodes) generally refer to a single one of those components or a plurality of those components.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The specific examples and descriptions herein are exemplary in nature and embodiments may be developed by those skilled in the art based on the material taught herein without departing from the scope of the present invention, which is limited only by the attached claims.

We claim:

1. A system, comprising:

an electroporation ablation device including:

- a single linear shaft including a linear distal portion positionable near a tissue wall, the linear shaft configured to be deflectable along one or more portions proximal to the linear distal portion to position the linear distal portion near the tissue wall, the linear shaft comprising a flexible shaft portion;
- a plurality of collinear electrodes disposed on the linear distal portion, the plurality of electrodes including:

a distal-most set of distal electrodes including a distal tip electrode disposed at a tip of the linear shaft and having a tip electrode length and an adjacent distal electrode having a first length and separated from the distal tip electrode by a distal spacing, wherein the tip electrode length is different from the first length; and a proximal-most set of proximal electrodes disposed proximal to the distal-most set, the proximal-most set of proximal electrodes including a first spacing separating an adjacent pair of proximal electrodes, the first spacing being substantially equal to the distal spacing;

the flexible shaft portion having a portion length of a second spacing separating the most distal proximal electrode of the proximal-most set of proximal electrodes from the most proximal distal electrode of the distal-most set of distal electrodes, at least one of the proximal electrodes from the adjacent pair having a second length, the first length being less than the second length, and the second spacing being greater than the first spacing and greater than the distal spacing;

an electromagnetic sensor disposed along the portion length of the flexible shaft portion, such that the electromagnetic sensor is positioned between the set of distal electrodes and the set of proximal electrodes; and a plurality of leads coupled to the plurality of electrodes, each lead having insulation configured to withstand a potential difference of at least about 700 V without dielectric breakdown; and a signal generator operatively coupled to the electroporation ablation device and configured to activate the distal electrodes with a first polarity and the proximal electrodes with a second polarity opposite the first polarity as an anode-cathode pair such that the plurality of electrodes generates a pulsed electric field that is capable of producing an ablation zone via irreversible electroporation in the tissue wall having a depth that is independent of an orientation of the linear distal portion relative to the tissue wall.

2. The system of claim 1, wherein the set of proximal electrodes are jointly wired using a first lead from the plurality of leads, and the set of distal electrodes is independently wired using a second lead from the plurality of leads.

3. The system of claim 1, wherein the ablation device further includes a pull wire configured to be actuated to deflect the linear shaft, the pull wire coupled to a location along the distal portion of the linear shaft.

4. The system of claim 1, wherein each of the first spacing and the second spacing is about 0.5 mm to about 12 mm.

5. The system of claim 4, wherein the ratio of the second spacing to the first spacing is between about 1 and about 20.

6. The system of claim 1, further comprising:

a tracking device configured to track a location of the distal portion of the linear shaft during positioning, the tracking device including a field generator configured to generate at least one of electric fields or magnetic fields, wherein the electromagnetic sensor is configured to receive a set of signals in response to the generated fields for determining the location of the distal portion of the linear shaft.

7. The system of claim 1, wherein the first length of the adjacent distal electrode is between about 1 mm and about 8 mm, and the second length of the at least one proximal electrode is between about 1 mm and about 6 mm.

8. The system of claim 1, wherein the set of proximal electrodes further includes a proximal electrode having a third length different from the second length.

9. The system of claim 1, wherein the signal generator is configured to activate the set of distal electrodes and the set of proximal electrodes to generate the pulsed electric field having a shape that is wider near the distal tip electrode than near the set of proximal electrodes.

10. An apparatus, comprising:

a single linear shaft including a linear distal portion positionable near a tissue wall, the linear shaft configured to be deflectable along one or more portions proximal to the linear distal portion to position the linear distal portion near the tissue wall, the linear shaft comprising a flexible shaft portion;

a plurality of electrodes disposed on the linear distal portion, the plurality of electrodes configured to generate a pulsed electric field with the plurality of electrodes being capable of producing an ablation zone in the tissue wall having a depth that is independent of an orientation of the linear distal portion relative to the tissue wall, the plurality of electrodes including:

a distal-most set of distal electrodes including a distal tip electrode, having a tip electrode length, disposed at a tip of the linear shaft and an adjacent distal electrode having a distal electrode length different from the tip electrode length and separated from the distal tip electrode by a distal spacing; and a proximal-most set of proximal electrodes disposed proximal to the distal-most set of distal electrodes, the proximal-most set of proximal electrodes including a proximal spacing separating an adjacent pair of proximal electrodes, the proximal spacing being greater than the distal spacing;

the flexible shaft portion having a portion length defining an electrode set spacing separating the most distal proximal electrode from the adjacent distal electrode, the most distal proximal electrode of the proximal-most set of proximal electrodes adjacent to the most proximal distal electrode of the distal-most set of distal electrodes, wherein the distal spacing and the proximal spacing are less than the electrode set spacing;

an electromagnetic sensor disposed along the portion length of the flexible shaft portion, such that the electromagnetic sensor is positioned between the set of distal electrodes and the set of proximal electrodes; and a plurality of leads coupled to the plurality of electrodes, each lead from the plurality of leads configured to deliver a voltage output having an amplitude of at least 700V to the plurality of electrodes (1) without dielectric breakdown of its corresponding insulation and (2) such that the set of distal electrodes are activated with a first polarity and the set of proximal electrodes are activated with a second polarity opposite the first polarity as an anode-cathode pair to collectively generate the pulsed electric field.

11. The apparatus of claim 10, wherein the set of proximal electrodes are jointly wired using a first lead from the plurality of leads, and the distal tip electrode and the adjacent distal electrode are jointly wired using a second lead from the plurality of leads.

12. The apparatus of claim 10, wherein the two proximal electrodes are jointly wired using a first lead from the plurality of leads, the distal tip electrode is independently wired using a second lead from the plurality of leads, and one or more distal electrodes disposed proximal to the distal tip electrode are independently or jointly wired using one or more third leads from the plurality of leads.

13. The apparatus of claim 10, wherein the linear shaft has a diameter of between about 1 mm and about 5 mm.

14. The apparatus of claim 10, wherein:

each proximal electrode from the set of proximal electrodes has a length of about 1 mm to about 6 mm, and each distal electrode from the set of distal electrodes has a length of about 1 mm to about 8 mm.

15. The apparatus of claim 10, wherein the ratio of the electrode set spacing to the proximal spacing is between about 1 and about 20.

16. The apparatus of claim 10, further comprising a pull wire including proximal and distal ends, the distal end of the pull wire coupled to the linear shaft at a location distal to the set of proximal electrodes and near the distal end of a portion of the linear shaft separating the most distal proximal electrode of the set of proximal electrodes from the most proximal distal electrode of the set of distal electrodes, the proximal end of the pull wire coupled to an actuation mechanism, the pull wire configured to be actuated via the actuation mechanism to deflect the linear shaft such that the portion of the linear shaft deflects with the deflection of the linear shaft.

17. The apparatus of claim 10, further comprising a pull wire including proximal and distal ends, the distal end of the pull wire coupled to the distal portion of the linear shaft, the proximal end of the pull wire coupled to an actuation mechanism, the pull wire configured to be actuated via the actuation mechanism so as to deflect the linear shaft.

18. The apparatus of claim 10, wherein the electromagnetic sensor, in response to at least one of electric fields or magnetic fields being generated by a field generator associated with a tracking device, is configured to receive a set of signals for determining a location of the distal portion.

19. The apparatus of claim 18, wherein a subset of the set of distal electrodes is configured to measure electrocardiogram (ECG) data.

20. The apparatus of claim 10, wherein each of the proximal, electrode set, and distal spacings are between about 0.5 mm and about 12 mm.

21. The apparatus of claim 10, wherein the proximal spacing is greater than the distal spacing.

22. A method, comprising:

positioning an ablation device including a single linear shaft in a cardiac chamber of a heart of a subject such that a linear distal portion of the linear shaft is near a first portion of a tissue wall with the linear shaft set at a first orientation to the first portion of the tissue wall, the linear shaft comprising a flexible shaft portion, the ablation device including a plurality of electrodes disposed on the linear distal portion and an electromagnetic sensor disposed at the flexible shaft portion, the plurality of electrodes including a distal-most set of distal electrodes, including a distal tip electrode having a distal tip length and an adjacent distal electrode having a distal electrode length different from the distal tip electrode length, and a proximal-most set of proximal electrodes, at least one adjacent pair of proximal electrodes of the set of proximal electrodes separated by a first spacing, the most distal proximal electrode of the set of proximal electrodes and the most proximal distal electrode of the set of distal electrodes separated by the flexible shaft portion having a portion length of a second spacing greater than the first spacing and devoid of electrodes of the plurality of electrodes, the most distal proximal electrode of the proximal-most set of proximal electrodes adjacent to the most proximal distal electrode of the distal-most set of distal electrodes, and the set of distal electrodes separated from each other by a distal spacing, the distal spacing less than each of the first spacing and the second spacing; and generating, using a signal generator, a first pulse waveform having a voltage amplitude of at least about 700 V;

delivering, while the linear distal portion is set at the first orientation, the first pulse waveform to the plurality of electrodes such that the set of distal electrodes are activated with a first polarity and the set of proximal electrodes are activated with a second polarity opposite the first polarity to collectively generate a pulsed electric field that produces an ablation zone in the first portion of the tissue wall;

positioning the ablation device in the cardiac chamber such that the linear distal portion is near a second portion of the tissue wall with the linear shaft set at a second orientation different from the first orientation;

generating, using the signal generator, a second pulse waveform having a voltage amplitude of at least about 700 V; and delivering, while the linear distal portion is set at the second orientation, the second pulse waveform to the plurality of electrodes such that the set of distal electrodes are activated with the first polarity and the set of proximal electrodes are activated with the second polarity as an anode-cathode pair to collectively generate a pulsed electric field that produces an ablation zone via irreversible electroporation in the second portion of the tissue wall having a depth that is approximately equal to a depth of the ablation zone produced in the first portion of the tissue wall.

23. The method of claim 22, wherein the cardiac chamber is an endocardial space of an atrium.

24. The method of claim 22, wherein each electrode from the plurality of electrodes has an insulated lead associated therewith, each insulated lead configured withstand a potential difference of at least about 700 V without dielectric breakdown of its corresponding insulation.

25. The method of claim 22, wherein the positioning of the linear shaft includes actuating a pull wire coupled to the distal portion to deflect the distal portion to steer the ablation device.

26. The method of claim 22, further comprising:

generating, using a field generator associated with a tracking device, at least one of electric fields or magnetic fields;

receiving, from a subset of the set of distal electrodes, a set of signals in response to the generated fields;

determining, based on the set of signals, a location of the distal portion of the linear shaft, the positioning of the linear shaft being guided by the location.

27. The method of claim 22, wherein each of the first, second, and distal spacings are between about 0.5 mm and about 12 mm.

28. The method of claim 22, wherein the ratio of the second spacing to the first spacing is between about 1 and about 20.

29. The method of claim 22, wherein:

each proximal electrode from the set of proximal electrodes has a length of about 1 mm to about 6 mm, and each distal electrode from the set of distal electrodes has a length of about 1 mm to about 8 mm.

30. The method of claim 22, wherein the linear shaft set at the first orientation is approximately normal to the first portion of the tissue wall, and the linear shaft set at the second orientation is obliquely opposed to the tissue wall.

* * * * *